(12) United States Patent
Lee et al.

(10) Patent No.: US 9,175,090 B2
(45) Date of Patent: Nov. 3, 2015

(54) METHODS OF USING AN ANTIBODY TO INHIBIT WNT-MEDIATED SIGNALING IN CANCER

(71) Applicant: Vanderbilt University, Nashville, TN (US)

(72) Inventors: Ethan Lee, Brentwood, TN (US); Pampee P. Young, Brentwood, TN (US); Josiane Eid, Nashville, TN (US); Robert Carnahan, Franklin, TN (US); Curtis Thorne, Dallas, TX (US); Kelly Meyers, Gallatin, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/446,073

(22) Filed: Jul. 29, 2014

(65) Prior Publication Data

US 2015/0086540 A1    Mar. 26, 2015

Related U.S. Application Data

(63) Continuation of application No. 13/460,242, filed on Apr. 30, 2012, now Pat. No. 8,790,650.

(60) Provisional application No. 61/480,218, filed on Apr. 28, 2011.

(51) Int. Cl.
| | |
|---|---|
| *A61K 39/395* | (2006.01) |
| *A61P 35/00* | (2006.01) |
| *C07K 16/28* | (2006.01) |
| *C07K 16/30* | (2006.01) |
| *A61K 45/06* | (2006.01) |
| *A61N 5/10* | (2006.01) |
| *A61K 39/00* | (2006.01) |

(52) U.S. Cl.
CPC ............ *C07K 16/30* (2013.01); *A61K 39/3955* (2013.01); *A61K 39/39558* (2013.01); *A61K 45/06* (2013.01); *A61N 5/10* (2013.01); *C07K 16/2863* (2013.01); *A61K 2039/505* (2013.01); *A61N 2005/1098* (2013.01); *C07K 2317/33* (2013.01); *C07K 2317/76* (2013.01)

(58) Field of Classification Search
None
See application file for complete search history.

(56) References Cited

U.S. PATENT DOCUMENTS

2011/0256127 A1    10/2011    Bourhis et al.

FOREIGN PATENT DOCUMENTS

WO    WO 2009/064944        5/2009
WO    WO 2009056634 A2 *    5/2009

OTHER PUBLICATIONS

Takahashi-Yanaga et al, 2010. Clinical Cancer Res. 16(12): 3153-3162.*
Minde et al, 2011. Molecular Cancer. 10:101, pp. 1-9, plus Supplement S1 (12 additional pages as printed).*
Angers and Moon, "Proximal events in Wnt signal transduction" *Nat. Rev. Cell Biol.*, 10(7):468-477, 2009.
Benjamini et al., *Immunology: A Short Course*, 2nd Ed., 1991. p. 40. Print.
Ettenberg et al., "Inhibition of tumorigenesis driven by different Wnt proteins requires blockade of distinct ligand-binding regions by LRP6 antibodies," *Proc. Natl Acad. Sci.*, 107(35):15473-15478, 2010.
Gong et al., "Wnt Isoform—specific interactions with coreceptor specify inhibition or potentiation of signaling by LRP6 antibodies," *PLOS One*, 5(9):e12682, 2010.
Kawano and Kypta, "Secreted antagonists of the Wnt signalling pathway," *J Cell Sci.*, 116(13):2627-2634, 2003.
NCBI Protein Database, Accession No. NP_002326.2, dated Jul. 7, 2013.
NCBI Protein Database, Accession No. NP_002327.2, dated May 26, 2013.
Office Action issued in U.S. Appl. No. 13/460,242, mailed Jul. 24, 2013.
Reya and Clevers, "Wnt signalling in stem cells and cancer," *Nature*, 434(7035):843-850, 2005.
Shtutman et al., "The cyclin D1 gene is a target of the beta-catenin/LEF-1 pathway," *Proc. Natl. Acad. Sci.*, 96(10):5522-5527, 1999.
Tahinci and Lee, "The interface between cell and developmental biology," *Curr. Opin. Genet. Dev.*, 14(4): 361-366, 2004.

* cited by examiner

*Primary Examiner* — Zachary Howard
(74) *Attorney, Agent, or Firm* — Parker Highlander PLLC

(57) ABSTRACT

The present invention is directed to monoclonal antibodies and fragments thereof directed to LRP5/6 that find use in the prevention and treatment of cardiac remodeling and cancer. Also disclosed are methods for using such monoclonal antibodies in the prevention and treatment of such diseases.

18 Claims, 13 Drawing Sheets

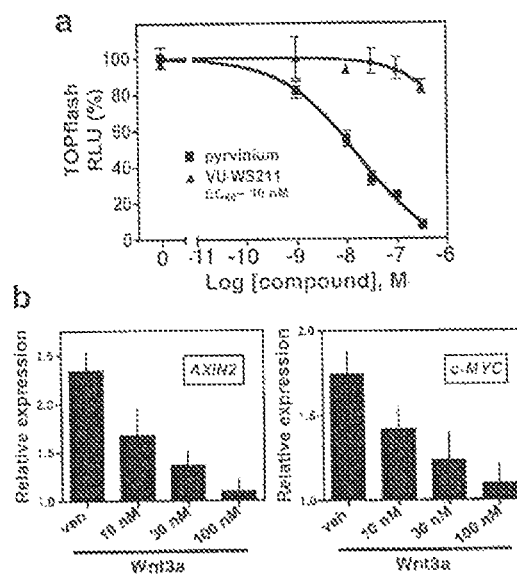
FIG. 2A-B

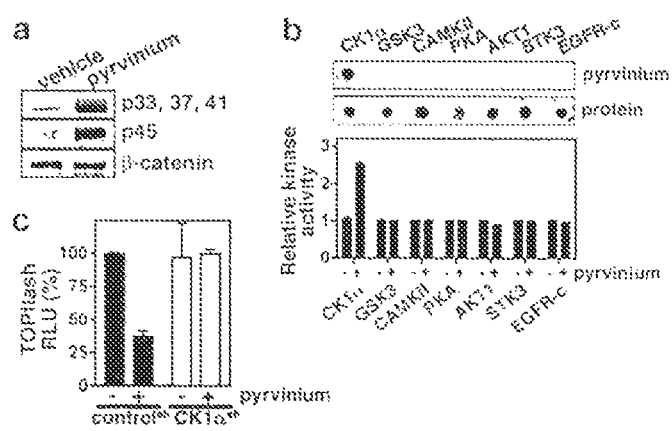
FIG. 3A-C

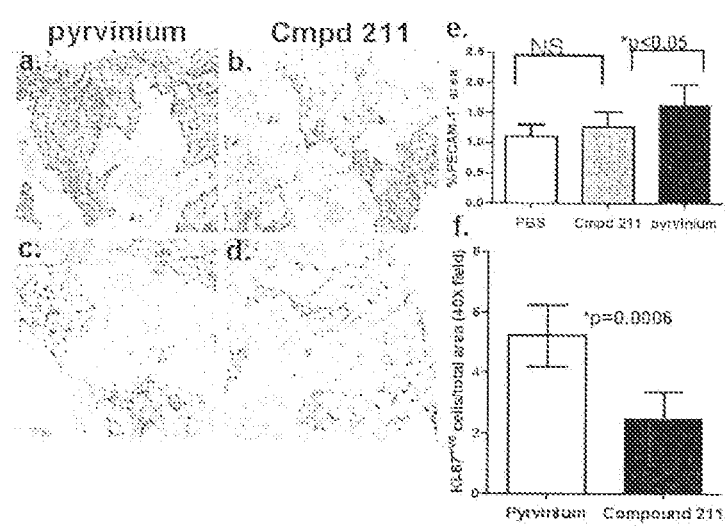
FIG. 4A-F

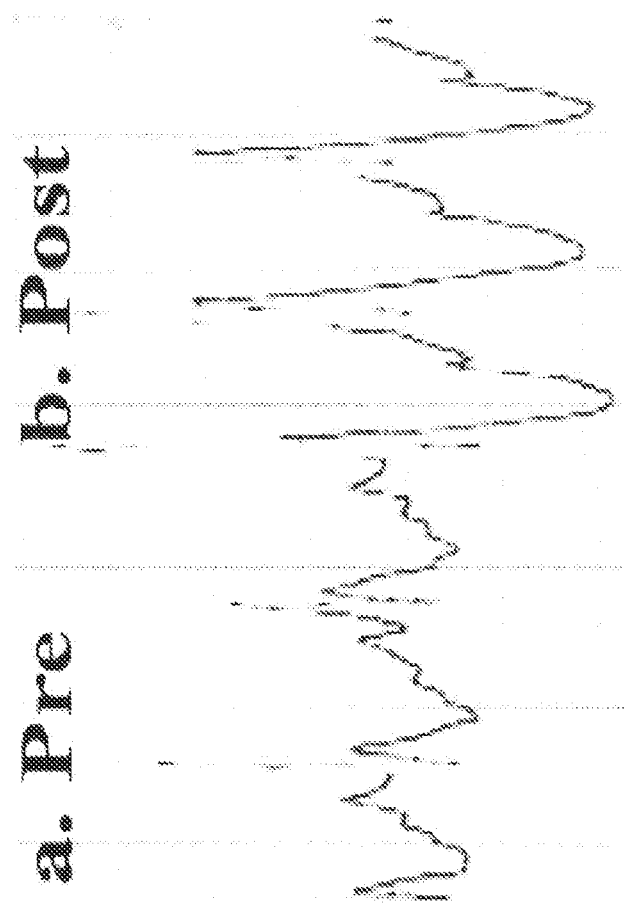
FIG. 5A-B

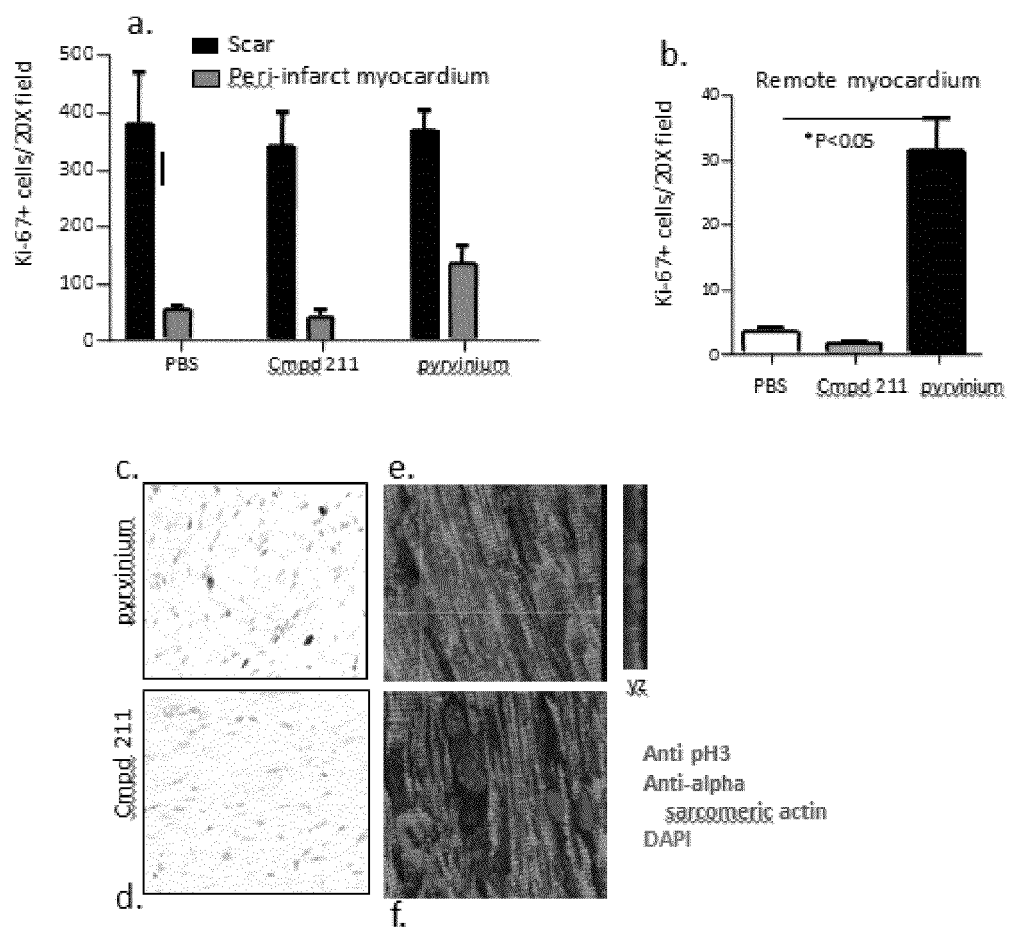
FIGS. 6A-F

FIGS. 8A-D

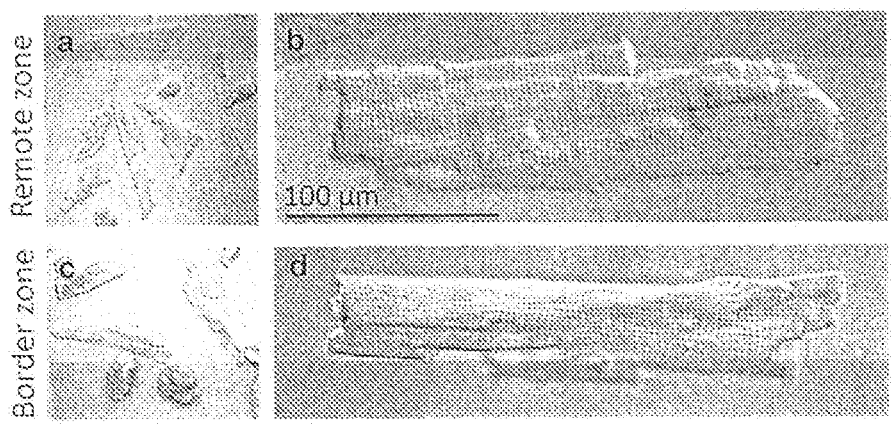
FIG. 10A-D

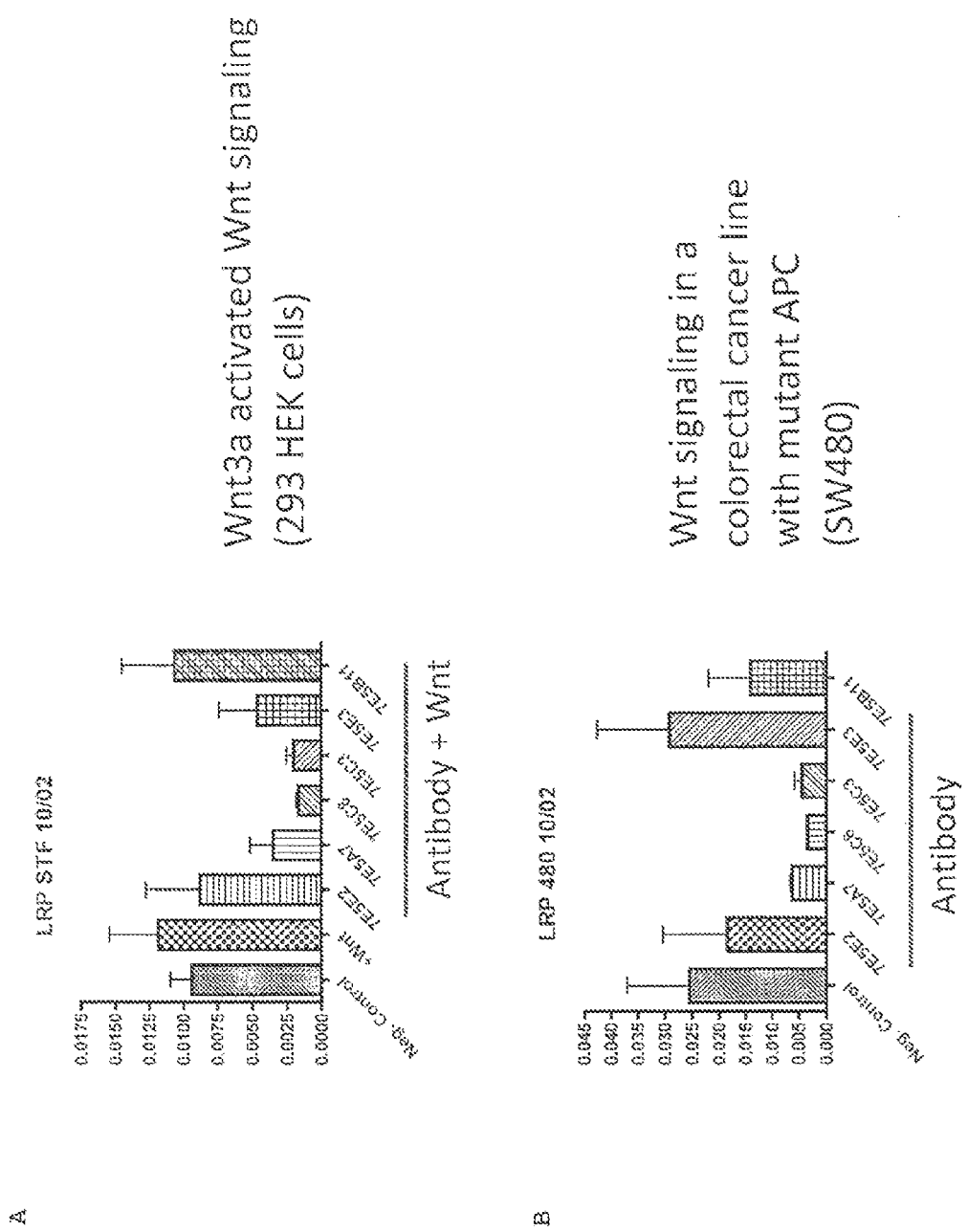
FIG. 11A-B

METHODS OF USING AN ANTIBODY TO INHIBIT WNT-MEDIATED SIGNALING IN CANCER

This application is a continuation of U.S. patent application Ser. No. 13/460,242, filed Apr. 30, 2012, now U.S. Pat. No. 8,790,650, which claims benefit of priority to U.S. Ser. No. 61/480,218, filed Apr. 28, 2011, the entire contents of each of which are hereby incorporated by reference.

This invention was made with government support under grant number 5RO1 GM081635-03 and 5RO1 HL088424-02, both awarded by the National Institutes of Health. The government has certain rights in the invention.

BACKGROUND OF THE INVENTION

1. Field of the Invention

The present invention relates generally to the fields of molecular biology, oncology and cardiology. More particularly, it concerns the development of monoclonal antibodies to LRP5/6 and for their use in the treatment of cardiovascular disease and cancer.

2. Background of the Invention

Myocardial infarction (MI) is a leading cause of disability and death. Each year, ~900,000 Americans experience a MI (American Heart Association, 2003; Topol, 2003). The management of patients with a healing MI includes revascularization during the first hours following infarction. The infarct injury affects the heart globally and induces a process termed "ventricular remodeling" that affects size, shape and function of the heart; this process is strongly linked with progression to heart failure and, ultimately, to morbidity and mortality. In fact, post-infarct remodeling, rather than hypertension and valvular disease, is currently considered to be the most common cause of heart failure (HF) (Id.).

The wound healing observed after MI parallels that seen in other tissues (Holmes et al., 2005; Buja and Entman, 1998; Cleutjens et al., 1999). The first phase is characterized by myocyte death (Holmes et al., 2005; Buja and Entman, 1998; Cleutjens et al., 1999). This process evokes an inflammatory response with disruption of the collagen network and deposition of granulation tissue (Tyagi et al., 1996). The altered post-infarct hemodynamics, in combination with its associated chemokine milieu, result in molecular changes in cardiomyocytes, fibroblasts and endothelial cells that lead to unfavorable remodeling through poorly-defined mechanisms.

After injury, myocyte numbers decrease (American Heart Association, 2003; Topol, 2003). It is well established that there is a direct correlation between the irreversible loss of cardiomyocytes and progression of cardiac dysfunction, adverse remodeling and eventual failure (American Heart Association, 2003; Topol, 2003; Cleutjens et al., 1999). Current therapies have reduced early mortality following MI but fail to address the primary cause of impaired function, the loss of myocytes (Topol, 2003; Sharpe, 2004; Sutton and Sharpe, 2000). Two strategies are being intensely investigated: stem cell transplantation and induction of myocyte proliferation.

Cardiomyocytes exit the cell cycle shortly after birth, and the adult mammalian heart is considered incapable of regeneration after injury (van Amerongen and Engel, 2008). In non-mammalian models (i.e. zebrafish) studies have demonstrated that lost myocardial tissue can be replenished by dedifferentiation and proliferation of differentiated cardiomyocytes (Kikuchi et al., 2010; Jopling et al., 2010). There are several lines of evidence that support the hypothesis that induction of cardiomyocyte proliferation can also promote mammalian heart regeneration. Analysis of human heart failure autopsy tissues indicate that individuals with early mortality have increased percentage of apoptotic myocytes and decreased expression of proliferation markers (Ki-67) compared to longer survivors (Swynghedauw, 1999). Forced cardiac expression of positive regulators of cell cycle progression (i.e. Cyclin A2 or Cyclin D2) in transgenic mice demonstrate enhanced cardiac function and improved remodeling following ischemic injury (van Amerongen and Engel, 2008; Chaudhry et al., 2004). Periostin and FGF1/p38 inhibitors promote myocyte proliferation and also improve cardiac repair (Engel et al., 2006; Kuhn et al., 2007). In summary, augmenting cardiomyocyte number by stimulating cardiomyocyte cell division may help cardiac regeneration following injury.

In spite of these promising reports, it is unlikely that inducing myocyte proliferation alone is sufficient to promote cardiac repair. For example, p38 inhibition (in the absence of FGF) was found to be insufficient to promote repair despite inducing myocyte proliferation (Engel et al., 2006). In addition, c-Myc-induced cardiomyocyte proliferation did not result in improved cardiac function (van Amerongen and Engel, 2008). Thus, other cellular effects and/or modulation of tissue stroma and vasculature may also be important. Finally, none of these extrinsic agents (i.e. periostin, FGF/p38 inhibitors) have been translated into feasible and effective therapies to repair the injured heart. Therefore, new and improved therapeutics for to promote cardiac repair and impede pathogenic cardiac remodeling are needed.

SUMMARY OF THE INVENTION

Thus, in accordance with the present invention, there is provided a method of inhibiting Wnt-mediated remodeling of cardiac tissue comprising administering to a subject identified as needing cardiac tissue remodeling an IgM antibody that binds to LRP5/6. Administering may comprise intravenous, intraarterial or intracardiac administration. The subject may be a human. The subject may have suffered an ischemic cardiac event with 24 hours of administering said antibody, within 12 hours of administering said antibody, within 4 hours of administering said antibody, or within 1 hour of administering said antibody. The cancer cell may have a mutation in APC, such as a lung cancer or colorectal cancer. The method may achieve one or more therapeutic endpoints such as reduced heart failure related hospitalizations, increased exercise capacity, reduced ventricular dilation, increased cardiac output, improved pump performance, reduced arrhythmia, reduced cardiac fibrosis, or reduced cardiac necrosis.

The antibody may be a monoclonal antibody, such as a humanized antibody. The antibody may bind the same epitope as the antibody produced by clone designation 7E5C8. The antibody may bind to an epitope of LRP6 found between residues 540 and 672, 701 and 850, and 920 or 1070 of SEQ ID NO: 6. The heavy chain sequence may be SEQ ID NO:2 or encoded by:

```
                                           (SEQ ID NO: 1)
CAGGTGCAGCTGAAGGAGTCAGGACCTGGCCTGGTGGCATCCTCACA

GAGCCTGTCCATCACATGCACTGTCTCTGGGTTCTCATTATCCAGAT

ATAGTGTACACTGGGTTCGCCAGCCTCCAGGAAAGGGTCTGGAGTGG

CTGGGAATGATATGGGGTGGTGGAAGCACAGACTATAATTCAGCTCT

CAAATCCAGACTGGGCATCAGCAAGGACAACTCCAAGAGCCAAGTTT
```

-continued

TCTTAAAAATGAACAGTCTGCAAACTGATGACACAGCCATGTACTAC

TGTGCCGGAACTGGTTCCTGGTTTGCTTACTGGGGCCAAGGGACTCT

GGTCACTGTCTCTGCA, and/or the light chain sequence may be SEQ ID NO: 4 or encoded by:

(SEQ ID NO: 3)
GACATCCAGATGACTCAGTCTCCAGCCTCCCTATCTGCATCTGTGGG

AGAAACTGTCACCATCACATGTCGAGCAAGTGGGAATATTCACAATT

ATTTAGCATGGTATCAGCAGAAACAGGGAAAATCTCCTCAGCTCCTG

GTCTATAATGCAAAAACCTTAGCAGATGGTGTGCCATCAAGGTTCAG

TGGCAGTGGATCAGGAACACAATATTCTCTCAAGATCAACAGCCTGC

AGCCTGAAGATTTTGGGAGTTATTACTGTCAACATTTTTGGAGTACT

CCGTGGACGTTCGGTGGAGGCACCAAGCTGGAAATCAAA.

The method may further comprise administering to said subject a second agent that treats one or more aspect of heart disease, such as a beta blocker, an iontrope, diuretic, ACE-I, AII antagonist, histone deacetylase inhibitor, a Ca(++)-blocker, or a TRP channel inhibitor. The second agent may be administered at the same time as said antibody, or after the antibody. The antibody may be administered more than once.

A method of inhibiting Wnt signaling in a cancer cell with a defect in Apc expression or activity comprising contacting said cancer cell with an IgM antibody that binds to LRP5/6. The cancer cell may be located in an animal subject. The antibody may be administered to said subject by intravenous, intraarterial, or intratumoral administration. The cancer cell may be a multi-drug resistant cell. The subject may suffer from recurrent cancer or metastatic cancer. The subject may suffer from sarcoma, colorectal cancer, gastric cancer, breast cancer, liver cancer, lymphoma, cervical cancer, uterine cancer, prostate cancer, lung cancer or melanoma. The cancer cell may have a mutation in APC, such as lung cancer or colorectal cancer. The method may achieve one or more therapeutic endpoints such as increased life span, improved stamina, improved quality of life, reduced hospital stay duration or frequency.

The antibody may be a monoclonal antibody, such as a humanized antibody. The antibody may bind the same epitope as the antibody produced by clone designation 7E5C8. The antibody may bind to an epitope of LRP6 found between residues 540 and 672, 701 and 850, or 920 and 1070 of SEQ ID NO: 6. The heavy chain sequence may be SEQ ID NO: 2 or encoded by:

(SEQ ID NO: 1)
CAGGTGCAGCTGAAGGAGTCAGGACCTGGCCTGGTGGCATCCTCACA

GAGCCTGTCCATCACATGCACTGTCTCTGGGTTCTCATTATCCAGAT

ATAGTGTACACTGGGTTCGCCAGCCTCCAGGAAAGGGTCTGGAGTGG

CTGGGAATGATATGGGGTGGTGGAAGCACAGACTATAATTCAGCTCT

CAAATCCAGACTGGGCATCAGCAAGGACAACTCCAAGAGCCAAGTTT

TCTTAAAAATGAACAGTCTGCAAACTGATGACACAGCCATGTACTAC

TGTGCCGGAACTGGTTCCTGGTTTGCTTACTGGGGCCAAGGGACTCT

GGTCACTGTCTCTGCA, and/or the light chain sequence may be SEQ ID NO: 4 or encoded by:

(SEQ ID NO: 3)
GACATCCAGATGACTCAGTCTCCAGCCTCCCTATCTGCATCTGTGGG

AGAAACTGTCACCATCACATGTCGAGCAAGTGGGAATATTCACAATT

ATTTAGCATGGTATCAGCAGAAACAGGGAAAATCTCCTCAGCTCCTG

GTCTATAATGCAAAAACCTTAGCAGATGGTGTGCCATCAAGGTTCAG

TGGCAGTGGATCAGGAACACAATATTCTCTCAAGATCAACAGCCTGC

AGCCTGAAGATTTTGGGAGTTATTACTGTCAACATTTTTGGAGTACT

CCGTGGACGTTCGGTGGAGGCACCAAGCTGGAAATCAAA.

The method may further comprise administering to said subject a second anticancer agent, such as a chemotherapeutic, a radiotherapeutic, hormone therapy, toxin therapy, or immunotherapy. The anti-cancer agent may be administered at the same time as said antibody, or before and/or after the antibody. The antibody may be administered more than once.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-B. (FIG. 2A) Pyrvinium inhibits TOPflash activation with an $IC_{50}$ of ~10 nM. HEK 293 STF (TOPflash) reporter cells were treated with Wnt3a-conditioned media and/or pyrvinium for 24 hours. Graph represents mean±s.e.m of TOPflash signal normalized to cell number (performed in quadruplicate). A structurally related compound, Cmpd 211 fails to inhibit TOPflash. (FIG. 2B) Pyrvinium decreases levels of endogenous Wnt target genes AXIN2 and c-MYC. Data shown represent mean of four independent amplification reactions, graphed as relative expression to unstimulated cells. Expression levels were normalized to β-actin mRNA. Error bars, RQ values with 95% confidence.

FIGS. 3A-C. CK1α is the intracellular target of pyrvinium. (FIG. 3A) Pyrvinium stimulates the phosphorylation of β-catenin in vitro. A kinase reaction was assembled in vitro with purified Axin, β-catenin, GSK3, and CK1 (100 nM each) in the absence or presence of pyrvinium (10 nM). Phosphorylation of β-catenin on GSK3 sites (p33,37,41) and the priming CK1α site (p45) was detected by immunoblotting. (FIG. 3B) Pyrvinium binds and activates CK1α but not kinases representative of other major branches of the kinome. Pyrvinium (10 nM) was incubated with purified recombinant kinases, and binding and kinase activities were assessed. Ligand-binding is based on the innate fluorescent property of pyrvinium and nitrocellulose immobilized protein. (FIG. 3C) Downregulating CK1α blocks the transcriptional responses to pyrvinium. A Jurkat cell line with inducible shRNA for CK1α (CK1α$^{sh}$) was incubated with pyrvinium (30 nM). Cells were treated with Wnt3a-conditioned media and lysates were assayed for TOPflash to assess Wnt signaling.

FIGS. 4A-F. Identification and organizational activity of granulation tissue as demonstrated in H&E stained slides generated in PVA sponges injected with pyrvinium (FIG. 4A) or Cmpd 211 (FIG. 4B). Representative sections stained with anti-CD31 (PECAM-1) to assess vascular density of sponge granulation tissue treated with pyrvinium (FIG. 4C) or Cmpd 211 (FIG. 4D). (FIG. 4E) Morphometric analysis of vascular density by anti-CD31 immunohistochemistry. Pictures from three fields of view from each section were assessed from four animals. The fraction of the field area positive for each was determined by point counting the total area comprising positive pixels divided by total area containing nucleated cells and the averages were graphed. (FIG. 4F) Graphed morphometric analysis of number of Ki-67+ cells (per high power; 40×) in pyrvinium or Cmpd 211 treated granulation tissue.

FIGS. 5A-D. Mouse MI model. Representative mouse EKG tracings pre (FIG. 5A) and post (FIG. 5B) coronary artery ligation. (FIG. 5C) Photomicrograph of Masson trichrome stain of a murine heart at 30 d showing a large area of transmural replacement fibrosis (infarction). Arrows mark lateral and posterior left ventricle (LV). LVIDD, LVIDS=LV internal diameter at systole and diastole, respectively. IVSS, IVSD=interventricular septal distance at systole and diastole, respectively. RV=right ventricle. (FIG. 5D) Graph of percent difference of LVIDD, LVIDS, IVSS and IVSD at d 7 and d 30 after treatment with a single (25 ml) injection of pyrvinium (n=22 animals injected; n=7 survived) or Cmpd 211 (n=6 injected; n=6 survived). A single injection of pyrvinium resulted in favorable remodeling of the mouse myocardium following infarction. Cardiac dimensions were obtained from 2-D guided M-mode images (100 frames/sec) and were read blinded using short axis and a parasternal long-axis views with the leading edge method. All echo measurements were averaged over 3 consecutive beats on unsedated mice at 7 and 30 days after infarction. Statistical significance assessed by the Wilcoxon rank sum test.

FIGS. 6A-F. Pyrvinium induces cardiomyocyte mitosis. Ki-67 positive nuclei in mouse heart evident within the scar and peri-infarct tissue (FIG. 6A) or remote myocardium (FIG. 6B) were quantified. *p<0.05 using One way ANOVA with Newman-keuls post-test. Representative immunostained sections of remote myocardium using anti-Ki-67 to show more mitotic nuclei in pyrvinium (FIG. 6C) vs. Cmpd 211-(FIG. 6D) treated hearts. (FIG. 6E) pH3-positive mononucleated, differentiated cardiomyocyte in pyrvinium-treated remote myocardium but not in Cmpd 211-treated tissue (FIG. 6F).

(FIG. 8A) 100 μl of plasma obtained from mice after treatment with 9.4 μg mLRP5/6 showed an ~5-fold and 2-fold greater inhibition of Wnt3a-mediated luciferase activity 48 and 72 hours, respectively, after drug administration compared to IgM injected controls. (FIG. 8B) Real time RT-PCR analysis of the Wnt pathway target genes, Axin 2 and Cyclin D, in heart homogenates obtained from mabLRP5/6 treated mice showed a ~2-fold reduction in Axin 2 and Cyclin D transcripts at 48 h compared to controls. Cycle thresholds for 18S mRNA transcripts were used to normalize between samples. n=4 mice analyzed at each time point for each cohort. Ki-67-positive cells in the heart (FIG. 8C) and pH3-positive mononucleated, differentiated cardiomyocytes in mabLRP5/6-treated remote myocardium (FIG. 8D).

FIGS. 10A-D. Isolation of viable, intact cardiomyocytes from infracted mouse hearts. Imaging was performed using an inverted microscope in the light-transmitted mode (20× oil immersion lens). XY images of low magnification fields (FIGS. 10A and C) showed myocyte yield obtained from both border and remote areas. High magnification images of respective individual myocytes (FIGS. 10B and D) were obtained by zooming-in on the cell of interest.

FIGS. 11A-B. Wnt activated signaling. (FIG. 11A) Wnt3a activated signaling in 293 HEK cells. (FIG. 11B) Wnt signaling in SW480 colorectal cancer cell line with mutant APC.

DESCRIPTION OF ILLUSTRATIVE EMBODIMENTS

Figure 1:
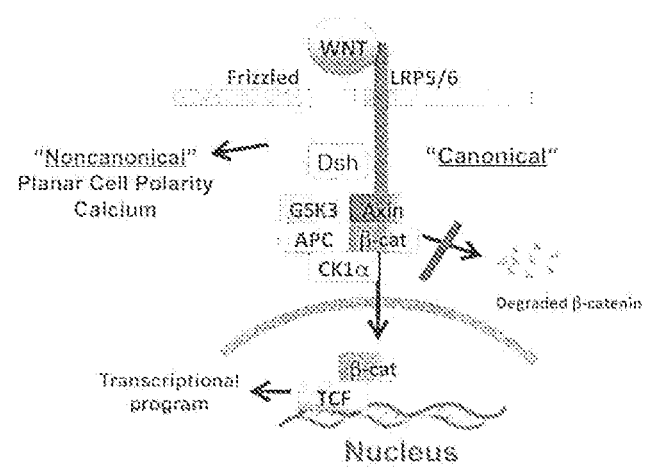
FIG. 1. Schematic of Wnt canonical (β-catenin) and non-canonical signaling pathways.

It is known that Wnt is disregulated in injured cardiac tissue. Building on their previous work with Wnt inhibitors in cancer, the inventors here show that administration of pyrvinium (a known Wnt inhibitor) into the myocardium showed more favorable ventricular remodeling compared to control in a mouse model of acute MI. Despite the fact that only a single injection of pyrvinium could be administered (due to its toxicity), there was a remarkable therapeutic benefit. These exciting preliminary data less to follow-up work focused on assessing the effect of more long-term therapeutic Wnt inhibition on myocardial repair and regeneration.

Although antibodies against LRP5/6 have been reported, there have been none described that inhibit Wnt signaling in vitro or in vivo. The inventors generated a well-tolerated LRP5/6 monoclonal antibody that inhibits Wnt signaling in vivo. Using this innovative tool, the inventors have begun to dissect pharmacologic inhibition of Wnt signaling over an extended time and establish anti-Wnt regimens for the treatment of heart disease. Therapeutic Wnt inhibition is likely to have significant potential in cardiac repair and regeneration and perhaps more broadly in repair of other tissues. Thus, the inventors' efforts to pioneer the use of an anti-LRP5/6 antibody to inhibit Wnt signaling will have important implications for regenerative medicine in general and, more specifically, for the treatment of MI. These and other aspects of the invention are described in greater detail below.

I. WNT SIGNALING AND LRP5/6

A. Wnt Signaling Through LRP5/6

Wnt ligands bind their cognate Frizzled-family receptors to regulate diverse biological processes including cell adhesion, proliferation, migration, and differentiation (Reya and Clevers, 2005; Widelitz, 2005; Shtutman et al., 1999; Tahinci and Lee, 2004). The central player of the "canonical" (Wnt/β-catenin) pathway is β-catenin, which is maintained at a low level in the cytoplasm by its association with a complex (axin, APC, GSK3β) that promotes its phosphorylation and targeted destruction (FIG. 1) (Reya and Clevers, 2005; Widelitz, 2005; Shtutman et al., 1999; Tahinci and Lee, 2004). Upon binding of Wnt by Frizzled and the LRP5 or 6 coreceptor (LRP5/6), the destruction complex is inhibited; β-catenin accumulates and trans-locates to the nucleus where it interacts with the Tcf/Lef1 transcription factors to regulate Wnt-specific gene expression (Reya and Clevers, 2005; Widelitz, 2005; Shtutman et al., 1999; Tahinci and Lee, 2004). "Non-canonical" Wnt signaling (e.g. planar cell polarity and intracellular calcium release (Reya and Clevers, 2005; Widelitz, 2005; Shtutman et al., 1999; Tahinci and Lee, 2004)) is less well understood at the molecular level.

Wnt signaling has been shown to be a major regulator of cardiogenesis (Cleutjens et al., 1999; Foley and Mercola, 2005; Salloway, 2003). Prior to gastrulation, Wnt/β-catenin signaling promotes cardiac differentiation whereas signaling during gastrulation inhibits heart formation (Cleutjens et al., 1999; Foley and Mercola, 2005; Salloway, 2003). Consistent with these studies, early treatment of mouse embryonic stem cells with Wnt3a stimulates mesoderm induction whereas late Wnt3a stimulation inhibits cardiac differentiation. Furthermore, the Wnt inhibitors Dickkopf-1 (Dkk-1) and secreted frizzled-related proteins (sFRPs) have been shown to induce cardiac differentiation of stem cells (Cleutjens et al., 1999; Salloway, 2003; Pandur et al., 2002)). Although these studies clearly demonstrate the importance of Wnt signaling in cardiac development, less is known about its role in adult cardiac repair. A recent study using Wnt (axin2-LacZ) reporter mice demonstrated that Wnt signaling is increased post-MI in cardiomyocytes of the border zone and remote area between 7-21 days whereas infiltrating CD45+ inflammatory cells showed Wnt activation between 3-7 days (Oerlemans et al., 2009). Hence, endogenous activation of the Wnt pathway occurs in the heart in cardiomyocytes and other heart cells and is evident just prior to the initiation of the remodeling phase (day 10-26) of murine infarct repair. The inventors hypothesize that infarct-induced Wnt activation contributes to adverse cardiac remodeling, a process that may be averted by Wnt inhibition. Several recent studies support this hypothesis. Transgenic mice in which β-catenin was downregulated in an alpha-MHC-restricted manner (i.e. resulting in lower cardiac Wnt signaling) demonstrated favorable ischemic remodeling (Zelarayan et al., 2008). Other groups reported functional deterioration after injury in mice expressing a stabilized β-catenin (i.e. activated Wnt signaling) in cardiomyocytes (Malekar et al., 2010; Baurand et al., 2007). Finally, the inventors and others have shown that mesenchymal stem cells overexpressing sFRP2, a Wnt inhibitor, reduced cardiomyocyte apoptosis (Mirotsou et al., 2007; Alfaro et al., 2008).

Several antagonists of the Wnt pathways have been characterized (Kawano and Kypta, 2003). One class, including sFRPs, binds and sequesters Wnts to inhibit both canonical and non-canonical Wnt signaling (Kawano and Kypta, 2003). Fusion of Frizzled8-cysteine rich domain (binds Wnt) to the human Fc domain inhibited Wnt signaling and teratocarcinoma growth in mice but has not been widely used in vivo possibly due to its low in vivo efficacy or issues of selectivity (DeAlmeida et al., 2007). The Dick class inhibits canonical Wnt signaling by binding to LRP5/LRP6 of the Wnt receptor complex ((Kawano and Kypta, 2003). Recently a novel class of small molecule Wnt inhibitors has been identified that act by inhibiting tankyrase, a poly(ADP-ribose) polymerase (Chen et al., 2009; Huang et al., 2009). These compounds have not been shown to be effective in vivo, possibly due to toxicity and/or bioavailability. The inventors previously identified a FDA-approved drug, pyrvinium, as a potent inhibitor of Wnt signaling that acts by binding and activating casein kinase 1α.

B. LRP5/6 Protein Sequences

The protein sequences for LRP5 and 6 are provided at accession nos. NP_002326.2 (SEQ ID NO:5) and NP_002327.2 (SEQ ID NO:6), respectively.

C. LRP5/6 NUCLEIC ACID SEQUENCES

The mRNAs for LRP5 and 6 are provided at accession nos. NM_002335 (SEQ ID NO:7) and NM_002336 (SEQ ID NO:8), respectively.

II. PRODUCING MONOCLONAL ANTIBODIES

A. General Methods

It will be understood that monoclonal antibodies binding to LRP5/6 will have utilities in several applications. These include the production of diagnostic kits for use in detecting and diagnosing disease. In these contexts, one may link such antibodies to diagnostic or therapeutic agents, or use them as capture agents or competitors in competitive assays. Means for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this invention were generated using the HMMA2.5 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). The hybridomas secreting the LRP5/6 antibodies in this invention were obtained by electrofusion.

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Invention

Antibodies according to the present invention may be defined, in the first instance, by their binding specificity combined with their functional attribute of blocking Wnt activity. Those of skill in the art, by assessing the binding affinity of a given antibody using techniques well known to those of skill in the art, and further assessing the affects on Wnt signaling, can determine whether such antibodies fall within the scope of the instant claims.

Another classification of antibody is by Ig type, and the present invention provides antibodies to LRP5/6 that are IgM. Still a further way of categorizing antibodies according to the present invention is by the specific epitopes or contact points on the antigen may define the antibody's specificity. Finally, the antibody may be defined in particular by reference to heavy/light chain variable region sequences.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into a Lonza pConIgG1 or pConK2 plasmid vector, transfected into 293 Freestyle cells or Lonza CHO cells, and antibodies were collected an purified from the CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

It may be desirable to "humanize" antibodies produced in non-human hosts in order to attenuate any immune reaction when used in human therapy. Such humanized antibodies may be studied in an in vitro or an in vivo context. Humanized antibodies may be produced, for example by replacing an immunogenic portion of an antibody with a corresponding, but non-immunogenic portion (i.e., chimeric antibodies). PCT Application PCT/US86/02269; EP Application 184,187; EP Application 171,496; EP Application 173,494; PCT Application WO 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985); also incorporated herein by reference. "Humanized" antibodies can alternatively be produced by CDR or CEA substitution. Jones et al. (1986); Verhoeyen et al. (1988); Beidler et al. (1988); all of which are incorporated herein by reference.

In related embodiments, the antibody is a derivative of the disclosed antibodies, e.g., an antibody comprising the CDR sequences identical to those in the disclosed antibodies (e.g., a chimeric, humanized or CDR-grafted antibody). In yet a further embodiment, the antibody is a fully human recombinant antibody.

Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present invention also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present invention may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Purification

In certain embodiments, the antibodies of the present invention may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens my be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. PASSIVE IMMUNIZATION USING LRP5/6 ANTIBODIES

A. Formulation and Administration

The present invention provides pharmaceutical compositions comprising anti-LRP5/6 antibodies and antigens for generating the same. Such compositions comprise a prophylactically or therapeutically effective amount of an antibody or a fragment thereof. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Passive transfer of antibodies, known as artificially acquired passive immunity, generally will involve the use of intravenous or intramuscular injections. Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the invention are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Cardiac Therapy

In one aspect of the present invention, there is provided a method inhibiting pathologic cardiac remodeling with LRP5/6 antibodies. The cardiac remodeling may be associated with various aspects of cardiac disease, such as cardiac hypertrophy, dilated cardiomyopathy and heart failure. The treatment would comprise provision of the antibody in any of the aforementioned routes when formulated appropriately for that delivery mode. In particular, intravenous injection (systemic or into the cardiac vasculature) and intracardiac (muscular) injection are envisioned. Repeated treatments (2, 3, 4, 5, 6, 7, 8, 9, 10, 15, 20, 25, 50 or more) over extended periods (24 hrs, 48 hrs, 72 hrs, 1 wk, 2 wk, 3 wk, 4 wk, 1 month, 2 months, 3 months, 4 months, 5 months, 6 months, 1 year or longer) are contemplated.

In certain embodiments, the antibodies of the present invention may be combined with "traditional" cardiac therapeutics. This process may involve administering to the patient the antibody of the present invention the other agent(s) at the same time. This may be achieved by use of a single pharmaceutical composition that includes both agents, or by administering two distinct compositions at the same time, wherein one composition includes the antibody of the present invention and the other includes the second agent(s). The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Non-limiting examples of such pharmacological therapeutic agents for heart disease that may be used in combination with the antibodies of the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent, surgery or a combination thereof. Various combinations may be employed, the antibody treatment of the present invention is "A" and the secondary treatment is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the secondary agent will follow general protocols for that drug, taking into account the toxicity, if any. It is expected that the treatment cycles would be repeated as necessary. Some non-limiting examples are provided below.

i. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol) or simvastatin (zocor).

d. Nicotinic Acid Derivatives

Non-limiting examples of nicotinic acid derivatives include nicotinate, acepimox, niceritrol, nicoclonate, nicomol and oxiniacic acid.

e. Thyroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

ii. Antiarteriosclerotics

Non-limiting examples of an antiarteriosclerotic include pyridinol carbamate.

iii. Antithrombotic/Fibrinolytic Agents

In certain embodiments, administration of an agent that aids in the removal or prevention of blood clots may be combined with administration of a modulator, particularly in treatment of atherscleroosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantin), heparin, sulfinpyranone (anturane) and ticlopidine (ticlid).

c. Thrombolytic Agents

Non-limiting examples of thrombolytic agents include tissue plaminogen activator (activase), plasmin, pro-urokinase, urokinase (abbokinase) streptokinase (streptase), anistreplase/APSAC (eminase).

iv. Blood Coagulants

In certain embodiments wherein a patient is suffering from a hemmorage or an increased likelyhood of hemmoraging, an agent that may enhance blood coagulation may be used. Non-limiting examples of a blood coagulation promoting agent include thrombolytic agent antagonists and anticoagulant antagonists.

a. Anticoagulant Antagonists

Non-limiting examples of anticoagulant antagonists include protamine and vitamine K1.

b. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

v. Antiarrythmic Agents

Non-limiting examples of antiarrythmic agents include Class I antiarrythmic agents (sodium channel blockers), Class II antiarrythmic agents (beta-adrenergic blockers), Class II antiarrythmic agents (repolarization prolonging drugs), Class IV antiarrythmic agents (calcium channel blockers) and miscellaneous antiarrythmic agents.

a. Sodium Channel Blockers

Non-limiting examples of sodium channel blockers include Class IA, Class IB and Class IC antiarrythmic agents. Non-limiting examples of Class IA antiarrythmic agents include disppyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrythmic agents include encainide (enkaid) and flecainide (tambocor).

b. Beta Blockers

Non-limiting examples of a beta blocker, otherwise known as a β-adrenergic blocker, a β-adrenergic antagonist or a Class II antiarrythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

c. Repolarization Prolonging Agents

Non-limiting examples of an agent that prolong repolarization, also known as a Class III antiarrhythmic agent, include amiodarone (cordarone) and sotalol (betapace).

d. Calcium Channel Blockers/Antagonist

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a miscellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

e. Miscellaneous Antiarrhythmic Agents

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

vi. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

e. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimefylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives. Non-limiting examples of arylethanolamine derivatives include amosulalol, bufuralol, dilevalol, labetalol, pronethalol, sotalol and sulfinalol.

Benzothiadiazine Derivatives. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothiazide, hydroflumethiazide, methyclothiazide, meticrane, metolazone, paraflutizide, polythiazide, tetrachlormethiazide and trichlormethiazide.

N-carboxyalkyl(peptide/lactam) Derivatives. Non-limiting examples of N-carboxyalkyl(peptide lactam) derivatives include alacepril, captopril, cilazapril, delapril, enalapril, enalaprilat, fosinopril, lisinopril, moveltipril, perindopril, quinapril and ramipril.

Dihydropyridine Derivatives. Non-limiting examples of dihydropyridine derivatives include amlodipine, felodipine, isradipine, nicardipine, nifedipine, nilvadipine, nisoldipine and nitrendipine.

Guanidine Derivatives. Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines. Non-limiting examples of hydrazines/phthalazines include budralazine, cadralazine, dihydralazine, endralazine, hydracarbazine, hydralazine, pheniprazine, pildralazine and todralazine.

Imidazole Derivatives. Non-limiting examples of imidazole derivatives include clonidine, lofexidine, phentolamine, tiamenidine and tolonidine.

Quanternary Ammonium Compounds. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives. Non-limiting examples of reserpine derivatives include bietaserpine, deserpidine, rescinnamine, reserpine and syrosingopine.

Suflonamide Derivatives. Non-limiting examples of sulfonamide derivatives include ambuside, clopamide, furosemide, indapamide, quinethazone, tripamide and xipamide.

g. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and Synephrine.

vii. Treatment Agents for Congestive Heart Failure

Non-limiting examples of agents for the treatment of congestive heart failure include anti-angiotension II agents, afterload-preload reduction treatment, diuretics and inotropic agents.

a. Afterload-Preload Reduction

In certain embodiments, an animal patient that can not tolerate an angiotension antagonist may be treated with a combination therapy. Such therapy may combine adminstration of hydralazine (apresoline) and isosorbide dinitrate (isordil, sorbitrate).

b. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticrnafen and urea.

c. Inotropic Agents

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

d. Antianginal Agents

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

viii. Surgical Therapeutic Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

C. Cancer Therapy

In one aspect of the present invention, there is provided a method inhibiting cancers and cancer cell growth with LRP5/6 antibodies. The inhibition may involve slowing a cancer's growth or metastasis, stopping its progression, reducing cancer burden or tumor size, or inducing apoptosis in cancers cells or necrosis in cancer tissue. The treatment would comprise provision of the antibody in an available route when formulated appropriately for that delivery mode. In particular, intravenous injection (systemic, regional to the tumor or into the tumor vasculature) and intratumoral injection are envisioned. Repeated treatments (2, 3, 4, 5, 6, 7, 8, 9, 10, 15, 20, 25, 50 or more) over extended periods (24 hrs, 48 hrs, 72 hrs, 1 wk, 2 wk, 3 wk, 4 wk, 1 month, 2 months, 3 months, 4 months, 5 months, 6 months, 1 year or longer) are contemplated.

In certain embodiments, the antibodies of the present invention may be combined with "traditional" anti-cancer therapeutics. This process may involve administering to the patient the antibody of the present invention the other agent(s) at the same time. This may be achieved by use of a single pharmaceutical composition that includes both agents, or by administering two distinct compositions at the same time, wherein one composition includes the antibody of the present invention and the other includes the second agent(s). The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Non-limiting examples of such therapeutic agents for cancer that may be used in combination with the antibodies of the present invention include an chemotherapeutics, radiotherapeutics, immunotherapeutics, hormonal therapy, toxin therapy, gene therapy cryotherapy, surgery or a combination thereof. Various combinations may be employed, the antibody treatment of the present invention is "A" and the secondary treatment is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the secondary agent will follow general protocols for that drug, taking into account the toxicity, if any. It is expected that the treatment cycles would be repeated as necessary. Some non-limiting examples are provided below.

i. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

ii. Radiotherapy

Factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

iii. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of certain poxvirus polypeptides would provide therapeutic benefit in the treatment of cancer.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to anticancer effects with immune stimulatory effects. Immune stimulating molecules also exist including: cytokines such as IL-2, IL-4, IL-12, GM-CSF, IFNγ, chemokines such as MIP-1, MCP-1, IL-8 and growth factors such as FLT3 ligand. Combining immune stimulating molecules, either as proteins or using gene delivery in combination with a tumor suppressor such as mda-7 has been shown to enhance anti-tumor effects (Ju et al., 2000).

As discussed earlier, examples of immunotherapies currently under investigation or in use are immune adjuvants (e.g., Mycobacterium bovis, Plasmodium falciparum, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (e.g., interferons α, β and γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. No. 5,830,880 and U.S. Pat. No. 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the poxvirus-related therapies described herein.

Passive Immunotherapy. A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie and Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

Active Immunotherapy. In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anti-carbohydrate antibodies.

Adoptive Immunotherapy. In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

iv. Gene Therapy

In yet another embodiment, the secondary treatment is a gene therapy. In one aspect, the gene therapy may seek to inhibit a protein product that induces cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

In a different embodiment, the gene therapy is a replacement therapy, where the gene product to be delivered restore normal growth regulation, inhibits cancer cell growth or even kills the cancer cells. The tumor suppressor oncogenes function to inhibit excessive cellular proliferation. The inactivation of these genes destroys their inhibitory activity, resulting in unregulated proliferation. The tumor suppressors p53, p16 and C-CAM are described below.

In addition to p53, which has been described above, another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1994; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

v. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

vi. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon α, β, and γ; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Recently, decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells (Marsters et al., 1999).

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

IV. ANTIBODY CONJUGATES

Antibodies of the present invention may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes and drugs, radionuclides, chelating agents, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938, 948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present invention concerns immunodetection methods for binding, purifying, removing, quantifying and otherwise generally detecting LRP5/6 and its associated antigens. While such methods can be applied in a traditional sense, another use will be in quality control and monitoring of vaccine and other virus stocks, where antibodies according to the present invention can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of LRP5/6 antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing LRP5/6, and contacting the sample with a first antibody in accordance with the present invention, as the case may be, under conditions effective to allow the formation of immunocomplexes.

These methods include methods for purifying LRP5/6 or related antigens from a sample. The antibody will preferably be linked to a solid support, such as in the form of a column matrix, and the sample suspected of containing the LRP5/6 or antigenic component will be applied to the immobilized antibody. The unwanted components will be washed from the column, leaving the LRP5/6 antigen immunocomplexed to the immobilized antibody, which is then collected by removing the organism or antigen from the column.

The immunobinding methods also include methods for detecting and quantifying the amount of LRP5/6 or related components in a sample and the detection and quantification of any immune complexes formed during the binding process. Here, one would obtain a sample suspected of containing LRP5/6 or its antigens, and contact the sample with an antibody that binds LRP5/6 or components thereof, followed by detecting and quantifying the amount of immune complexes formed under the specific conditions. In terms of antigen detection, the biological sample analyzed may be any sample that is suspected of containing LRP5/6 or LRP5/6 antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to LRP5/6 or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the LRP5/6 or LRP5/6 antigen is added to the wells. After binding and washing to remove non-specifically bound immune complexes, the bound antigen may be detected. Detection may be achieved by the addition of another anti-LRP5/6 antibody that is linked to a detectable label. This type of ELISA is a simple "sandwich ELISA." Detection may also be achieved by the addition of a second anti-LRP5/6 antibody, followed by the addition of a third antibody that has binding affinity for the second antibody, with the third antibody being linked to a detectable label.

In another exemplary ELISA, the samples suspected of containing the LRP5/6 or LRP5/6 antigen are immobilized onto the well surface and then contacted with the anti-LRP5/6 antibodies of the invention. After binding and washing to remove non-specifically bound immune complexes, the bound anti-LRP5/6 antibodies are detected. Where the initial anti-LRP5/6 antibodies are linked to a detectable label, the immune complexes may be detected directly. Again, the immune complexes may be detected using a second antibody that has binding affinity for the first anti-LRP5/6 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present invention contemplates the use of competitive formats. This is particularly useful in the detection of LRP5/6 antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors proposes the use of labeled LRP5/6 monoclonal antibodies to determine the amount of LRP5/6 antibodies in a sample. The basic format would include contacting a known amount of LRP5/6 monoclonal antibody (linked to a detectable label) with LRP5/6 antigen or particle. The LRP5/6 antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

3. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

4. Immunodetection Kits

In still further embodiments, the present invention concerns immunodetection kits for use with the immunodetection methods described above. As the LRP5/6 antibodies are generally used to detect LRP5/6 or LRP5/6 antigens, the antibodies will be included in the kit. The immunodetection kits will thus comprise, in suitable container means, a first antibody that binds to LRP5/6 or LRP5/6 antigen, and optionally an immunodetection reagent.

In certain embodiments, the LRP5/6 antibody may be prebound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the LRP5/6 or LRP5/6 antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection or blow-molded plastic containers into which the desired vials are retained.

VI. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Pyrvinium Inhibits Wnt Signaling

The inventors developed a biochemical assay using *Xenopus laevis* egg extract that recapitulates Axin and β-catenin turnover in response to addition of recombinant Wnt co-receptor (LRP6) (Cselenyi et al., 2008). In *Xenopus* egg extract, β-catenin is robustly degraded and Axin is stable. In the presence of LRP6, however, β-catenin degradation is inhibited and Axin degradation is stimulated. Using this system (with β-catenin fused to firefly luciferase and Axin fused to *Renilla luciferase* as reporters for protein levels), they performed a high-throughput screen to identify small molecules that reverse the effects of recombinant LRP6. The inventors identified an FDA-approved antihelminthic compound (pyrvinium) that promotes β-catenin degradation and inhibits Axin degradation in *Xenopus* extract. Using a TOP-flash reporter cell line (293HEK STF) in which luciferase is under the control of the TCF/Lef1 promoter, the inventors found that pyrvinium inhibits Wnt signaling with an $IC_{50}$ of ~10 nM in contrast to a control compound with a similar structure (Cmpd 211; FIG. 2A). Inhibition of Wnt signaling was further confirmed by real-time RT-PCR of endogenous Wnt target genes, Axin2 and c-MYC (FIG. 2B).

Mechanism of Pyrvinium Action.

To test whether pyrvinium acts directly on the β-catenin degradation complex, the inventors assembled an in vitro reaction consisting of purified GSK3, CK1α, Axin, and β-catenin and tested the effect of pyrvinum on β-catenin phosphorylation, a prerequisite for its degradation. Addition of pyrvinium to this system resulted in a dramatic increase in β-catenin phosphorylation, including sites specific for GSK3 and CK1α (FIG. 3A). Pyrvinium enhanced phosphorylation of Tau by CK1α, but had no observable effect on GSK3 activity (data not shown). To demonstrate specificity for CK1α, the inventors tested the capacity of pyrvinium to bind and activate representative kinases from major branches of the kinase superfamily. Of the kinases tested, they observed pyrvinium binding and activation of CK1α alone (FIG. 3B). If pyrvinium inhibits Wnt signaling via activation of CK1α, loss of CK1α should block the effects of pyrvinium on Wnt signaling. The inventors used a cell line with reduced CK1α levels due to inducible expression of shRNA against CK1α. They found that, in contrast to control cells, pyrvinium failed to inhibit TOPflash activity in shRNA-CK1α cells (FIG. 3C). These results indicate that the effects of pyrvinium on Wnt signaling are mediated by its activation of CK1α.

Wnt Inhibition by Pyrvinium Promotes Advanced, Vascularized Granulation Tissue in a Murine Model.

The deposition of granulation tissue after wounding is a critical step in tissue regeneration (Inoue et al., 1998). To determine the effect of Wnt inhibition in promoting both the quantity and quality of granulation tissue deposition (Davidson et al., 1985; Li et al., 2005), the inventors implanted polyvinyl alcohol (PVA) sponge discs (isolate granulation tissue from epithelial reformation) subcutaneously beneath the ventral panniculus carnosus in adult mice. Each mouse (n=6) was implanted with four sponges and sacrificed on day 14. Each sponge was injected on day (d) 2, 4, 6 and 8, 10, and 12 with 50 μl of the following agents reconstituted in PBS/1% albumin: Sponge 1 and 2 received 200 nM pyrvinium, sponge 3 received 200 nM Cmpd 211, and sponge 4 received vehicle alone. A range of pyrivnium doses (25-300 nM) was tested to determine the optimal dose that enhances proliferation of mesenchymal stem cells (MSCs) in vitro (data not shown). FIGS. 4A-F is a representative H&E stained section obtained from the same mouse of a sponge receiving pyrvinium or Cmpd 211. Granulation tissue from sponges treated with Cmpd 211 or vehicle (data not shown) exhibited loose, disorganized architecture. In contrast, granulation tissue from pyrvinium-treated sponges exhibited more cellularity and better tissue organization. Vascular density of the granulation tissue was greater in pyrvinium-treated sponges compared to Cmpd 211-treated sponges when histologic sections were assessed by anti-PECAM-1 staining (marks endothelial cells) (FIGS. 4C-E). Cellular proliferation of granulation tissue was assessed by immunostaining for the nuclear protein Ki-67, a marker for proliferation (FIG. 4F). Pyrvinium treatment of PVA sponges resulted in approximately 2.5-fold increase in cell proliferation of the resultant granulation tissue (FIG. 4F).

A Single Administration of Pyrvinium Results in Improved Cardiac Remodeling in a Murine Acute Myocardial Infarct Model.

Myocardial infarcts were induced in male C57Bl/6 mice by coronary ligation (FIG. 5) as previously described (Alfaro et al., 2008). 30 min post-ligation, the inventors injected 200 nM of pyrvinium or Cmpd 211 at the junction of viable and infarcted tissue. A large number (15) of mice treated with intracardiac pyrvinium experienced lethal toxicity and died within the first 24 hours. Animals that survived beyond the first 48 hours demonstrated similar activity and growth pattern as the control animals. Toxicity associated with pyrvinium was anticipated as IV or IP injection of pyrvinium at levels high enough to achieve Wnt-inhibitory plasma levels resulted in death within 24-48 hours in most mice.

Figure 5C:
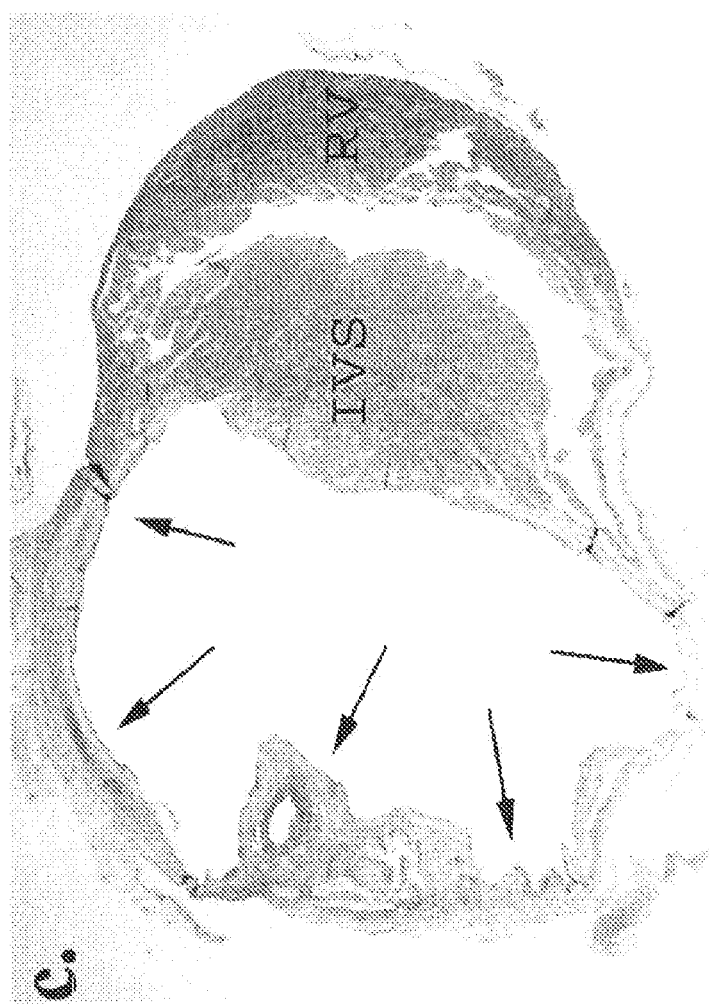
Figure 5D:
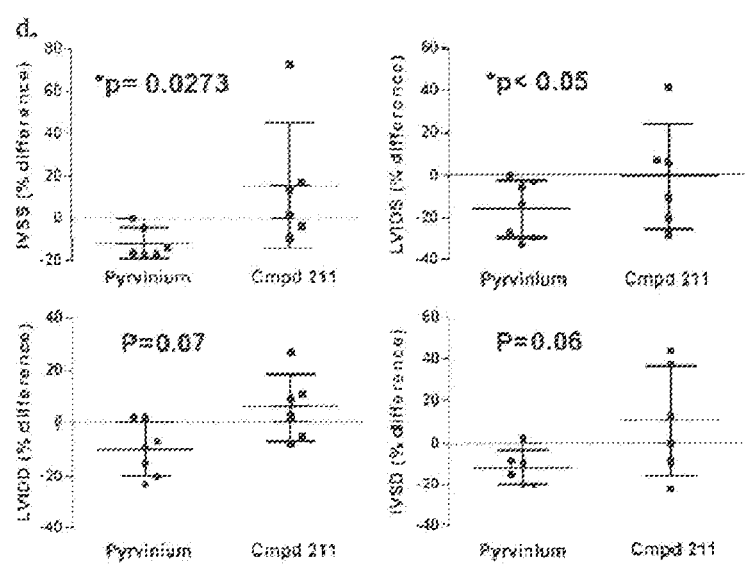

Left coronary artery ligation produced infarcts in the anterolateral wall of the LV (FIG. 5). Ventricular remodeling and cardiac functional parameters will be assessed by echo. All four (LVIDD, LVIDS, IVSS, and IVSD) dimensional parameters (as analyzed by percentage difference between days 7 and 30 echo measurements) were smaller in the pyrvinium-treated recipients compared to those receiving Cmpd 211, providing strong support for post-injury Wnt inhibition as a means to prevent adverse chamber remodeling (FIG. 5). In particular, the percent difference between LVIDD, LVIDS were statistically significant (p<0.05). The data set available thus far remains small and additional numbers are necessary. The average difference in fractional shortening of pyrvinium-treated animals between days 7 and 30 was 22.3+5.2 vs 15.4+ 8.3 (p<0.05). Comparison of infarct size between the two cohorts also did not reflect any statistically significant differences (data not shown). This observation, along with the absence of functional or anatomic difference between the two cohorts at day 7, provides greater evidence that pyrvinium did not acutely affect the extent of the infarct. Because the inventors were limited to a single administration of pyrvinium after injury, they are unable to confidently assess the effect of Wnt inhibition on cardiac function/infarct size.

Wnt Inhibition by Pyrvinium Increases Cardiomyoctye Mitosis in the Postmitotic Myocardium.

Mammalian cardiomyocytes irreversibly withdraw from the cell cycle soon after birth and undergo terminal differentiation. DNA synthesis, karyokinesis, and cytokinesis do not occur (or occur at very low levels) in adult murine cardiomyocytes 3 weeks after birth (Beinlich and Morgan, 1993; Simpson, 1989). Therefore, cardiac injury causes permanent myocardial loss and cardiac dysfunction. The inventors tested the hypothesis that favorable remodeling mediated by pyrvinium may be through inducing mitosis of adult cardiomyoctyes. Proliferation was assessed by immunostaining for Ki-67. While the numbers of Ki-67-positive cells were similar in the scar of both control Cmpd 211- and pyrvinium-treated animals, in the peri-infarct and, strikingly, in the remote myocardium, the numbers of Ki-67-positive cells were significantly higher in the pyrvinium-treated hearts (FIGS. 6A-D). Phosphorylation of histone 3 (pH3) on Ser 10 is an established cellular marker for chromosome condensation during mitotic prophase (van Amerongen and Engel, 2008). The inventors immunostained for pH3 and performed confocal microscopy to assess the effect of Wnt inhibition on the mitotic status of cardiomyocytes. pH3+ (red) cells exhibited a differentiated phenotype as indicated by striations and expression of α-sarcomeric actin (green). Reconstruction of optical sections enabled us to assign pH3-positive nuclei unequivocally to cardiomyocytes (side panel). Importantly, pyrvinium did not induce myocyte proliferation in sham-operated animals that received a single intramyocardial injection into LV apex (data not shown).

Summary.

These data show that pyrvinium, a potent and specific small molecule inhibitor of canonical Wnt signaling, promoted better organized and vascularized granulation tissue in vivo compared to control. The inventors show that mice treated with peri-infarct intramuscular administration of pyrvinium demonstrated significantly more favorable LV remodeling 30 d post-MI compared to a control compound. Remarkably, this effect was observed after only a single dose of intramuscular administration of the Wnt inhibitor following injury. These data further suggest that the cellular basis of Wnt-inhibitor-mediated remodeling is, in part, due to induction of myocyte mitosis. These findings highlight the potential of Wnt inhibition to treat MI and the need for a safe and effective therapeutic Wnt inhibitor to better dissect the effect of Wnt inhibition on cardiac repair and regeneration.

Example 2

Figure 7:
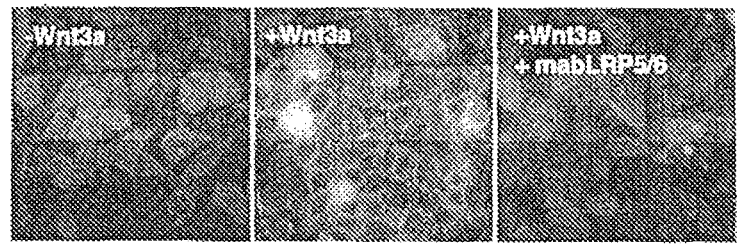
FIG. 7. mabLRP6 inhibits Wnt3a-induced nuclear accumulation of β-catenin. RKO cells were treated with Wnt3a in the presence or absence of 300 pg/ml mabLRP6 for 24 hours. Cells were fixed and immunostained for β-catenin (green). DAPI (blue) stains DNA.

Development of an Anti-LRP5/6 Antibody that Acts as a Potent Inhibitor of Canonical Wnt Signaling In Vitro Although the Wnt coreceptors, LRP5/6, are required for canonical Wnt signaling, they are not believed to be required for non-canonical signaling (Angers and Moon, 2009). In order to generate monoclonal antibodies against LRP5/6, three 15 kDa fragments encoding evolutionarily conserved domains of human LRP6 (also conserved in LRP5) were expressed and purified from bacteria. Recombinant proteins were used to inoculate BALB/c mice. Hybridoma lines were initially screened by ELISA for reactivity, and positive lines (1,500 clones) were tested for their ability to inhibit Wnt3a-mediated activation of the Wnt pathway using the TOPflash reporter cell line. Approximately 150 cell lines were identified that produced antibodies with anti-Wnt signaling activity. Nearly all of these lines were unstable, however, and failed to produce inhibitory antibodies over time. One line, mabLRP5/6, was stable and was further characterized. mabLRP5/6 was were found to blocked nuclear accumulation of β-catenin in response to Wnt3a and to inhibit Wnt signaling with an $IC_{50}$~200 pg/ml (FIG. 7; data not shown).

mabLRP5/6 Inhibits Canonical Wnt Signaling In Vivo and Induces Cardiomyoctye Mitosis Post-MI.

Figure 8:
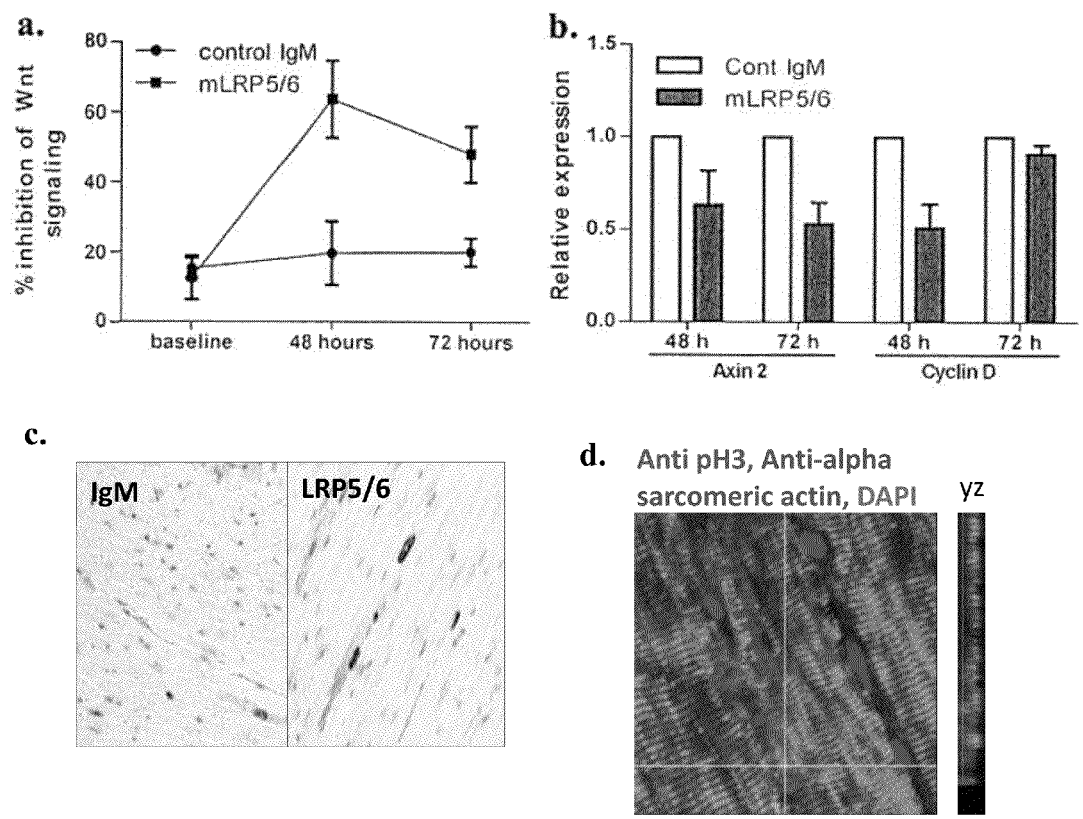
FIGS. 8A-D. mabLRP5/6 effectively and safely inhibits canonical Wnt signaling in mice and induces cardiomyocyte mitosis. The canonical Wnt signaling pathway was assessed using luciferase activity in HEK cells stably transfected with TOPflash reporter. Cells were treated with recombinant Wnt 3a to activate Wnt signaling.

To evaluate whether mabLRP5/6 inhibits Wnt-mediated transcription in vivo, the inventors injected 3 groups of mice IV with increasing amounts of mabLRP5/6 (2.3 μg, 4.7 μg or 9.4 μg, n=3 in each group) or control IgM. Mice were sacrificed after 48 hours and serum and tissue samples were obtained. Plasma (50 μl) from mice treated with 4.7 and 9.4 μg of mabLRP5/6 (FIGS. 8A-D, only 9.4 μg shown) inhibited Wnt signaling in the TOPflash reporter cell line (in contrast to control) at 48 and 72 hours to varying but significant degrees. To determine if IV treatment with mabLRP5/6 resulted in Wnt-inhibitory effects in heart tissue, the inventors assessed transcript levels of the Wnt target genes, Axin 2 and Cyclin D that are upregulated by canonical Wnt signaling (hence Wnt inhibition should decrease transcript levels). Heart tissues from treated animals were homogenized and total RNA isolated for real time RT-PCR analysis (Young et al., 2005). Both Axin2 and Cyclin D transcripts were downregulated ~2-fold in the hearts of mabLRP5/6-treated animals at 48 hours. The effect on Axin 2 transcript persisted at 72 hours after a single administration. To obtain evidence that mabLRP5/6 has cellular effects on post-MI myocardium, the inventors analyzed by immuno-histology paraffin-embedded sections from male mice treated with either IgM or mabLRP5/6 12 hours prior to induction of acute MI and then sacrificed 14 days later (n=1 for each condition). They identified >3-fold higher Ki-67$^+$ and pH3$^+$ cells in the remote LV from the mabLRP5/6-treated mouse compared to the control IgM-treated mouse (FIGS. 8C-D).

Preliminary Studies Show Improved Myocardial Ventricular Function and Adverse Remodeling with Post-Infarct High Dose mMABLRP5/6.

Figure 9:
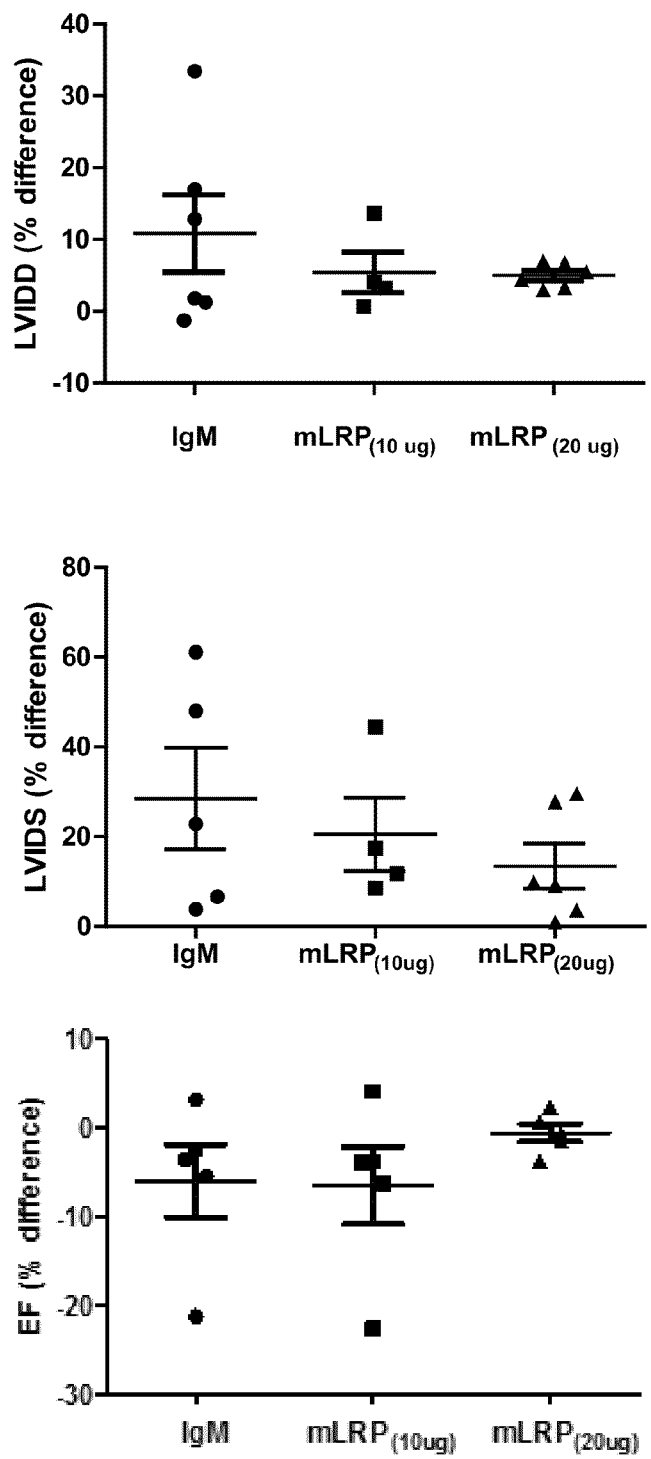
FIG. 9. Effect of low and high dose of mabLRP5/6 administered post infarct as compared to IgG control. LVIDD and LVIDS to represent cardiac remodeling, and EF, ejection fraction, as a measurement of cardiac function, were determined by echocardiography and are plotted as percentage difference values (mean±SD) between 7 and 30 days after infarct.

The inventors initiated studies to determine the effectiveness of mMABLRP5/6 on repair and regeneration of injured myocardium using an mouse acute myocardial infarct model. Myocardial infarcts were induced in 8-week old male C57Bl/6 mice (30-31 kg) by coronary ligation (FIG. 9) as previously described (Alfaro et al., 2008). At the time of infarction, the inventors administered 10 μg or 20 μg of mabLRP5/6 in 100 μl PBS or the same amount of IgM as control, intravenously by tail vein injection. The mice received a second dose of mabLRP5/6 or control antibody 72 hours after infarct to maintain at least 50% Wnt inhibition activity in the plasma through 7 days post infarct (data not shown). Ventricular remodeling and cardiac function were analyzed by echocardiography pre-infarct and at 7 and 30 days post MI. Ventricular function was reflected by ejection fraction (EF). LV internal dimension diastolic (LVIDD) and LV internal dimension systolic (LVIDS) reflected remodeling of the infarcted ventricle (FIG. 1). The percentage difference in LVIDD between day 7 and day 30 showed a dose-dependent trend towards less adverse remodeling in animals receiving when compared with the control IgM; 5.36±0.83 (high dose) as compared to 6.23+2.3 (low dose) vs. 10.9±5.79 (IgM). Additionally, the percentage difference in LVIDS between day 7 and day 30 was reduced in a dose-dependent manner in animals treated with 20 μg of mMABLRP5/6 when compared with 10 μg dose or control IgM. During this time, EF also decreased less in the high dose mabLRP5/6-treated animals, whereas those treated with low dose or IgM control exhibited similar decrease (~6%). The data set available thus far remains too small to demonstrate statistical significance. However, these data show a dose-dependent trend in mice receiving mabLRP5/6 towards both improved ventricular function and remodeling parameters. These data look promising and support the inventors' hypothesis that pharmacologic Wnt inhibition using mabLRP5/6 prevents adverse remodeling and preserves ventricular function. Additional numbers of animals as well as histologic myocardial analysis and high-resolution visual sonics studies are pending to determine infarct size and elucidate effects of mabLRP5/6 on endogenous cellular myocardial repair.

Feasibility of isolating sufficient numbers of viable cardiomyocytes from infarct border zone as well remote myocardium post infarct. Myocardial infarction were induced in mice as described above. Infarcted mice were sacrificed 4 months later and the hearts removed for myocyte isolation. The tissue in the area around the infarct, which included 2 mm of muscle form the scar, was dissected and designated "border zone." The area distant to the infarct was designated "remote zone"; both tissues were processed to isolate viable cardiomyocytes as previously reported (Knollmann et al.; 2003). The myocyte yield was around 40% intact myocytes from the borderzone tissue, and higher (50-70%) from the remote tissue. Immunoblot for tubulin showed a significant reduction in tubulin protein in the borderzone myocytes compared to the remote myocytes (Knollmann et al.; 2003). Isolated myocytes were fixed with a solution containing paraformaldehyde (final concentration 2%), and permeabilized with Triton-X (0.01%). After that, the cells were resuspended in PBS azide and kept at 4° C. until they were imaged (FIGS. 10A-B). These data demonstrate the capability to isolate sufficient numbers of viable, adult cardiomyocytes from distinct anatomical areas following experimental infarction.

Summary.

These studies indicate that inhibition of Wnt signaling by injection of pyrvinium promotes better-vascularized wound repair tissue. The inventors show that administration of pyrvinium post-MI promoted left ventricular remodeling and stimulated cardiomyocyte proliferation only in infarcted hearts. Hence, Wnt signaling is likely activated in a subset of cardiomyocytes following MI. To date, there are no drugs or biologics in the clinic that inhibit the Wnt pathway. In vivo toxicity associated with currently available small molecule inhibitors (including pyrvinium) of the Wnt pathway is a major limitation in the ability to test their therapeutic potential (Chen et al., 2009; Huang et al., 2009). Thus, development of mabLRP5/6 as a potent in vivo Wnt inhibitor with minimal toxicity represents a major breakthrough. These data indicate that pretreatment with mabLRP5/6 significantly induced cardiomyocyte mitosis after infarct. The inventors thus predict that Wnt inhibition by mabLRP5/6 will enhance cardiac repair and regeneration following MI.

The inventors examined effects of antibodies on Wnt signaling activated by recombinant Wnt3a, which was added to the media, and effects of antibodies on Wnt signaling in a colorectal cancer line (SW480) that has constitutively active Wnt signaling due to a mutation in the tumor suppressor, APC. They found that antibodies were able to inhibit Wnt signaling in both cases (FIGS. 11A-B). This was unexpected because the APC mutation is downstream of the LRP6 receptor, to which the antibody is directed. This finding suggests that antibodies against LRP6 could be used to treat colorectal cancers with mutations in APC, which are found in ~80 of all colorectal cancers. As a control, the inventors have also used lithium activation, which activates the pathway downstream of the receptor and in a different manner, and the antibody does not inhibit Wnt signaling.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 5,856,456
U.S. Pat. No. 5,880,270
"Antibodies: A Laboratory Manual," Cold Spring Harbor Press, Cold Spring Harbor, N.Y., 1988.
Abbondanzo et al., Am. J. Pediatr. Hematol. Oncol., 12(4), 480-489, 1990.
Alfaro et al., Proc. Nat'l Acad. Sci. USA 105, 18366-18371, 2008.
Allred et al., Arch. Surg., 125(1), 107-113, 1990.
American Heart Association, In: Heart Disease and Stroke Statistics—2004 Update, Dallas, Tex.: 2003.
Angers and Moon, Nature Rev. Mol. Cell Biol., 10:468-477, 2009.
Arap et al., Cancer Res., 55(6):1351-1354, 1995.
Atherton et al., Biol. of Reproduction, 32, 155-171, 1985.
Austin-Ward and Villaseca, Revista Medica de Chile, 126(7): 838-845, 1998.
Bajorin et al., J. Clin. Oncol., 6(5):786-792, 1988.
Bakhshi et al., Cell, 41(3):899-906, 1985.
Baurand et al., Circ Res., 100:1353-1362, 2007.
Beidler et al., J. Immunol., 141(11):4053-4060, 1988.
Beinlich and Morgan, Mol. Cell Biochem., 119:3-9, 1993.
Brown et al., J. Immunol. Meth., 12; 130(1), 111-121, 1990.
Buja and Entman, Circ., 98:1355-1357, 1998.
Bukowski et al., Clinical Cancer Res., 4(10):2337-2347, 1998.
Caldas et al., Cancer Res., 54:3568-3573, 1994.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
Capaldi et al., Biochem. Biophys. Res. Comm., 74(2):425-433, 1977.
Chaudhry et al. J. Biol. Chem., 279:35858-35866, 2004.

Chen et al., *Nat. Chem. Biol.*, 5:100-107, 2009.
Cheng et al., *Cancer Res.*, 54(21):5547-5551, 1994.
Christodoulides et al., *Microbiology*, 144(Pt 11):3027-3037, 1998.
Cleary and Sklar, *Proc. Natl. Acad. Sci. USA*, 82(21):7439-7443, 1985.
Cleary et al., *J. Exp. Med.*, 164(1):315-320, 1986.
Cleutjens et al., *Cardiovascular Res.*, 44:232-241, 1999.
Cselenyi et al., *Proc. Natl. Acad. Sci. USA*, 105:8032-8037, 2008.
Davidson et al., *J. Cell Biol.*, 100:1219-1227, 1985.
Davidson et al., *J. Immunother.*, 21(5):389-398, 1998.
De Jager et al., *Semin. Nucl. Med.* 23(2), 165-179, 1993.
DeAlmeida et al., *Cancer Res.*, 67:5371-5379, 2007.
Dholakia et al., *J. Biol. Chem.*, 264, 20638-20642, 1989.
Dillman, *Cancer Biother. Radiopharm.*, 14(1):5-10, 1999.
Doolittle and Ben-Zeev, *Methods Mol. Biol.*, 109, 215-237, 1999.
Engel et al., *Proc. Natl. Acad. Sci. USA*, 103:15546-15551, 2006.
EP Application 125,023
EP Application 171,496
EP Application 173,494
EP Application 184,187
Foley and Mercola, *Genes Dev.*, 19:387-396, 2005.
Gefter et al., *Somatic Cell Genet.*, 3:231-236, 1977.
Goding, In: *Monoclonal Antibodies: Principles and Practice*, 2d ed., Orlando, Fla., Academic Press, 60-61, 65-66, 71-74, 1986.
Gulbis and Galand, *Hum. Pathol.* 24(12), 1271-1285, 1993.
Hanibuchi et al., *Int. J. Cancer*, 78(4):480-485, 1998.
Hellstrand et al., *Acta Oncol.*, 37(4):347-353, 1998.
Holmes et al., *Annu. Rev. Biomed. Eng.*, 7:223-253, 2005.
Huang et al., *Nature*, 461:614-620, 2009.
Hui and Hashimoto, *Infection Immun.*, 66(11):5329-5336, 1998.
Hussussian et al., *Nat. Genet.*, 8(1):15-21, 1994.
Ii et al., *Circ.*, 111:1114-1120, 2005.
Inoue et al., *Wound Repair Regen.*, 6:213-222, 1998.
Irie and Morton, *Proc. Natl. Acad. Sci. USA*, 83(22):8694-8698, 1986.
Irie et al., *Lancet.*, 1(8641):786-787, 1989.
Jones et al., *Nature*, 321:522-525, 1986.
Jopling et al., *Nature*, 464:606-611, 2010.
Ju et al., *Gene Ther.*, 7(19):1672-1679, 2000.
Kamb et al., *Nat. Genet.*, 8(1):23-26, 1994.
Kamb et al., *Science*, 2674:436-440, 1994.
Kawano and Kypta, *J. Cell Science*, 116:2627-2634, 2003.
Kerr et al., *Br. J. Cancer*, 26(4):239-257, 1972.
Khatoon et al., *Ann. of Neurology*, 26, 210-219, 1989.
Kikuchi et al., *Nature*, 464:601-606, 2010.
King et al., *J. Biol. Chem.*, 269, 10210-10218, 1989.
Knollmann et al., *Circ. Res.* 92, 428-436, 2003.
Kohler and Milstein, *Eur. J. Immunol.*, 6, 511-519, 1976.
Kohler and Milstein, *Nature*, 256, 495-497, 1975.
Kuhn et al., *Nature Med.*, 13:962-969, 2007.
Kyte and Doolittle, *J. Mol. Biol.*, 157(1):105-132, 1982.
Malekar et al., *Hypertension*, 55:939-945, 2010.
Marsters et al., *Recent Prog. Horm. Res.*, 54:225-234, 1999.
Mirotsou et al., *Proc. Natl. Acad. Sci. USA*, 104:1643-1648, 2007.
Mitchell et al., *Ann. NY Acad. Sci.*, 690:153-166, 1993.
Mitchell et al., *J. Clin. Oncol.*, 8(5):856-869, 1990.
Mori et al., *Cancer Res.*, 54(13):3396-3397, 1994.
Morrison, *Science*, 229(4719):1202-1207, 1985.
Morton et al., *Arch. Surg.*, 127:392-399, 1992.
Nakamura et al., In: *Enzyme Immunoassays: Heterogeneous and Homogeneous Systems*, Chapter 27, 1987.
Nobori et al., *Nature*, 368(6473):753-756, 1994.
Oerlemans et al., *Circ.*, 120:S847, 2009.
Okamoto et al., *Proc. Natl. Acad. Sci. USA*, 91(23):11045-11049, 1994.
Orlow et al., *Cancer Res*, 54(11):2848-2851, 1994.
O'Shannessy et al., *J. Immun. Meth.*, 99, 153-161, 1987.
Owens and Haley, *J. Biol. Chem.*, 259, 14843-14848, 1987.
Pandur et al., *Nature*, 418:636-641, 2002.
PCT Application PCT/US86/02269
PCT Application WO 86/01533
Pietras et al., *Oncogene*, 17(17):2235-2249, 1998.
Posner et al., *Hybridoma* 6, 611-625, 1987.
Potter and Haley, *Meth. Enzymol.*, 91, 613-633, 1983.
Qin et al., *Proc. Natl. Acad. Sci. USA*, 95(24):14411-14416, 1998.
Ravindranath and Morton, *Intern. Rev. Immunol.*, 7: 303-329, 1991.
Reya and Clevers, *Nature*, 434:843-850, 2005.
Rosenberg et al., *Ann. Surg.* 210(4):474-548, 1989.
Rosenberg et al., *N. Engl. J. Med.*, 319:1676, 1988.
Salloway, *Cardiovascular Res.*, 58:264-277, 2003.
Serrano et al., *Nature*, 366:704-707, 1993.
Serrano et al., *Science*, 267(5195):249-252, 1995.
Sharpe, *Am. J. Cardiol.*, 93:17B-20B, 2004.
Shaw et al., *J. Natl. Cancer Inst.*, 80(19):1553-1559, 1988.
Shtutman et al., *Proc. Natl. Acad. Sci. USA*, 11:5522-5527, 1999.
Simpson, *Annu. Rev. Physiol.*, 51:189-202, 1989.
Sun et al., *J. Steroid Biochem.*, 26(1):83-92, 1987.
Sutton and Sharpe, *Circ.*, 101:2981-2988, 2000.
Swynghedauw, *Physiol Rev.*, 70:215-262, 1999.
Tahinci and Lee, *Curr. Opin. Genet. Dev.*, 14:361-366, 2004.
Tang et al., *J. Biol. Chem.*, 271:28324-28330, 1996.
Topol, *Circ.* 108:1116-13, 2003.
Tsujimoto and Croce, *Proc. Natl. Acad. Sci. USA*, 83(14):5214-5218, 1986.
Tsujimoto et al., *Science*, 228(4706):1440-1443, 1985.
Tyagi et al., *Mol. Cell Biochem.*, 155:13-21, 1996.
van Amerongen and Engel, *J. Cell Mol. Med.*, 12:2233-2244, 2008.
Verhoeyen et al., *Science*, 239(4847):1534-1536, 1988.
Wawrzynczak & Thorpe, *Cancer Treat Res.*, 37:239-51, 1988.
Widelitz, *Growth Factors*, 23:111-116, 2005.
Wood et al., *J. Clin. Lab. Immunol.*, 17(4):167-171, 1985.
Young et al., *Circ.*, 111:2382-2390, 2005.
Zelarayan et al., *Proc. Natl. Acad. Sci. USA*, 105:19762-19767, 2008.

What is claimed is:

1. A method of inhibiting Wnt signaling in a cancer cell with a defect in Adenomatous polyposis coli tumor suppressor (APC) expression or activity comprising contacting said cancer cell with an antibody that binds to low density lipoprotein receptor-related protein 5 and/or 6 (LRP5/6) and has heavy chain complementarity determining regions from SEQ ID NO: 2 and light chain complementarity determining regions from SEQ ID NO: 4.

2. The method of claim 1, wherein the antibody is a monoclonal antibody.

3. The method of claim 2, wherein the monoclonal antibody is a humanized antibody.

4. The method of claim 1, wherein the cancer cell is a multi-drug resistant cell.

5. The method of claim 1, wherein the cancer cell has a mutation in APC.

6. The method of claim 5, wherein the cancer cell is a lung cancer cell or a colorectal cancer cell.

7. The method of claim 1, wherein the antibody has a heavy chain sequence of SEQ ID NO: 2 and a light chain sequence of SEQ ID NO:4.

8. The method of claim 1, wherein said antibody is contacted more than once.

9. The method of claim 1, wherein said cancer cell is located in an animal subject.

10. The method of claim 9, wherein said antibody is administered to said subject by intravenous, intraarterial, or intratumoral administration.

11. The method of claim 9, wherein the subject suffers from recurrent cancer.

12. The method of claim 9, wherein the subject suffers from metastatic cancer.

13. The method of claim 9, wherein the subject suffers from sarcoma, colorectal cancer, gastric cancer, breast cancer, liver cancer, lymphoma, cervical cancer, uterine cancer, prostate cancer, lung cancer or melanoma.

14. The method of claim 9, further comprising administering to said subject a second anti-cancer therapy.

15. The method of claim 14, wherein the second anti-cancer therapy is a chemotherapeutic, a radiotherapeutic, hormone therapy, toxin therapy, or immunotherapy.

16. The method of claim 14, wherein the second anti-cancer therapy is administered at the same time as said antibody.

17. The method of claim 14, wherein the second anti-cancer therapy is administered before and/or after the antibody.

18. The method of claim 9, wherein said method achieves one or more therapeutic endpoints selected from the group consisting of increased life span, improved stamina, improved quality of life, reduced hospital stay duration and frequency.

* * * * *

SEQUENCE LISTING

<160> NUMBER OF SEQ ID NOS: 8

<210> SEQ ID NO 1
<211> LENGTH: 345
<212> TYPE: DNA

<213> ORGANISM: Homo sapiens
<220> FEATURE:
<221> NAME/KEY: CDS
<222> LOCATION: (1)..(345)

<400> SEQUENCE: 1

| | | | | | | | | | | | | | | | | |
|---|---|---|---|---|---|---|---|---|---|---|---|---|---|---|---|---|
| cag | gtg | cag | ctg | aag | gag | tca | gga | cct | ggc | ctg | gtg | gca | tcc | tca | cag | 48 |
| Gln | Val | Gln | Leu | Lys | Glu | Ser | Gly | Pro | Gly | Leu | Val | Ala | Ser | Ser | Gln | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agc | ctg | tcc | atc | aca | tgc | act | gtc | tct | ggg | ttc | tca | tta | tcc | aga | tat | 96 |
| Ser | Leu | Ser | Ile | Thr | Cys | Thr | Val | Ser | Gly | Phe | Ser | Leu | Ser | Arg | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| agt | gta | cac | tgg | gtt | cgc | cag | cct | cca | gga | aag | ggt | ctg | gag | tgg | ctg | 144 |
| Ser | Val | His | Trp | Val | Arg | Gln | Pro | Pro | Gly | Lys | Gly | Leu | Glu | Trp | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| gga | atg | ata | tgg | ggt | ggt | gga | agc | aca | gac | tat | aat | tca | gct | ctc | aaa | 192 |
| Gly | Met | Ile | Trp | Gly | Gly | Gly | Ser | Thr | Asp | Tyr | Asn | Ser | Ala | Leu | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| tcc | aga | ctg | ggc | atc | agc | aag | gac | aac | tcc | aag | agc | caa | gtt | ttc | tta | 240 |
| Ser | Arg | Leu | Gly | Ile | Ser | Lys | Asp | Asn | Ser | Lys | Ser | Gln | Val | Phe | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aaa | atg | aac | agt | ctg | caa | act | gat | gac | aca | gcc | atg | tac | tac | tgt | gcc | 288 |
| Lys | Met | Asn | Ser | Leu | Gln | Thr | Asp | Asp | Thr | Ala | Met | Tyr | Tyr | Cys | Ala | |
| | | | 85 | | | | | 90 | | | | | 95 | | | |

| | | | | | | | | | | | | | | | | |
|---|---|---|---|---|---|---|---|---|---|---|---|---|---|---|---|---|
| gga | act | ggt | tcc | tgg | ttt | gct | tac | tgg | ggc | caa | ggg | act | ctg | gtc | act | 336 |
| Gly | Thr | Gly | Ser | Trp | Phe | Ala | Tyr | Trp | Gly | Gln | Gly | Thr | Leu | Val | Thr | |
| | | | 100 | | | | | 105 | | | | | 110 | | | |

| | | | |
|---|---|---|---|
| gtc | tct | gca | 345 |
| Val | Ser | Ala | |
| | | 115 | |

<210> SEQ ID NO 2
<211> LENGTH: 115
<212> TYPE: PRT
<213> ORGANISM: Homo sapiens

<400> SEQUENCE: 2

| | | | | | | | | | | | | | | | |
|---|---|---|---|---|---|---|---|---|---|---|---|---|---|---|---|
| Gln | Val | Gln | Leu | Lys | Glu | Ser | Gly | Pro | Gly | Leu | Val | Ala | Ser | Ser | Gln |
| 1 | | | | 5 | | | | | 10 | | | | | 15 | |

| | | | | | | | | | | | | | | | |
|---|---|---|---|---|---|---|---|---|---|---|---|---|---|---|---|
| Ser | Leu | Ser | Ile | Thr | Cys | Thr | Val | Ser | Gly | Phe | Ser | Leu | Ser | Arg | Tyr |
| | | | 20 | | | | | 25 | | | | | 30 | | |

| | | | | | | | | | | | | | | | |
|---|---|---|---|---|---|---|---|---|---|---|---|---|---|---|---|
| Ser | Val | His | Trp | Val | Arg | Gln | Pro | Pro | Gly | Lys | Gly | Leu | Glu | Trp | Leu |
| | | 35 | | | | | 40 | | | | | 45 | | | |

| | | | | | | | | | | | | | | | |
|---|---|---|---|---|---|---|---|---|---|---|---|---|---|---|---|
| Gly | Met | Ile | Trp | Gly | Gly | Gly | Ser | Thr | Asp | Tyr | Asn | Ser | Ala | Leu | Lys |
| | 50 | | | | | 55 | | | | | 60 | | | | |

| | | | | | | | | | | | | | | | |
|---|---|---|---|---|---|---|---|---|---|---|---|---|---|---|---|
| Ser | Arg | Leu | Gly | Ile | Ser | Lys | Asp | Asn | Ser | Lys | Ser | Gln | Val | Phe | Leu |
| 65 | | | | 70 | | | | | 75 | | | | | 80 | |

| | | | | | | | | | | | | | | | |
|---|---|---|---|---|---|---|---|---|---|---|---|---|---|---|---|
| Lys | Met | Asn | Ser | Leu | Gln | Thr | Asp | Asp | Thr | Ala | Met | Tyr | Tyr | Cys | Ala |
| | | | 85 | | | | | 90 | | | | | 95 | | |

| | | | | | | | | | | | | | | | |
|---|---|---|---|---|---|---|---|---|---|---|---|---|---|---|---|
| Gly | Thr | Gly | Ser | Trp | Phe | Ala | Tyr | Trp | Gly | Gln | Gly | Thr | Leu | Val | Thr |
| | | | 100 | | | | | 105 | | | | | 110 | | |

| | | |
|---|---|---|
| Val | Ser | Ala |
| | | 115 |

<210> SEQ ID NO 3
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 3

```
gac atc cag atg act cag tct cca gcc tcc cta tct gca tct gtg gga      48
Asp Ile Gln Met Thr Gln Ser Pro Ala Ser Leu Ser Ala Ser Val Gly
1               5                   10                  15 gaa act gtc acc atc aca tgt cga gca agt ggg aat att cac aat tat      96
Glu Thr Val Thr Ile Thr Cys Arg Ala Ser Gly Asn Ile His Asn Tyr
            20                  25                  30 tta gca tgg tat cag cag aaa cag gga aaa tct cct cag ctc ctg gtc     144
Leu Ala Trp Tyr Gln Gln Lys Gln Gly Lys Ser Pro Gln Leu Leu Val
        35                  40                  45 tat aat gca aaa acc tta gca gat ggt gtg cca tca agg ttc agt ggc     192
Tyr Asn Ala Lys Thr Leu Ala Asp Gly Val Pro Ser Arg Phe Ser Gly
    50                  55                  60 agt gga tca gga aca caa tat tct ctc aag atc aac agc ctg cag cct     240
Ser Gly Ser Gly Thr Gln Tyr Ser Leu Lys Ile Asn Ser Leu Gln Pro
65                  70                  75                  80 gaa gat ttt ggg agt tat tac tgt caa cat ttt tgg agt act ccg tgg     288
Glu Asp Phe Gly Ser Tyr Tyr Cys Gln His Phe Trp Ser Thr Pro Trp
                85                  90                  95 acg ttc ggt gga ggc acc aag ctg gaa atc aaa                         321
Thr Phe Gly Gly Gly Thr Lys Leu Glu Ile Lys
            100                 105
```

<210> SEQ ID NO 4
<211> LENGTH: 107
<212> TYPE: PRT
<213> ORGANISM: Homo sapiens

<400> SEQUENCE: 4

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys
            100                 105
```

<210> SEQ ID NO 5
<211> LENGTH: 1615
<212> TYPE: PRT
<213> ORGANISM: Homo sapiens

<400> SEQUENCE: 5

```
Met Glu Ala Ala Pro Gly Pro Trp Pro Leu Leu Leu Leu Leu
1               5                   10                  15

Leu Leu Leu Leu Ala Leu Cys Gly Cys Pro Ala Pro Ala Ala Ala Ser
            20                  25                  30

Pro Leu Leu Leu Phe Ala Asn Arg Arg Asp Val Arg Leu Val Asp Ala
        35                  40                  45

Gly Gly Val Lys Leu Glu Ser Thr Ile Val Val Ser Gly Leu Glu Asp
    50                  55                  60
```

```
Ala Ala Ala Val Asp Phe Gln Phe Ser Lys Gly Ala Val Tyr Trp Thr
 65                  70                  75                  80

Asp Val Ser Glu Glu Ala Ile Lys Gln Thr Tyr Leu Asn Gln Thr Gly
                 85                  90                  95

Ala Ala Val Gln Asn Val Val Ile Ser Gly Leu Val Ser Pro Asp Gly
                100                 105                 110

Leu Ala Cys Asp Trp Val Gly Lys Lys Leu Tyr Trp Thr Asp Ser Glu
            115                 120                 125

Thr Asn Arg Ile Glu Val Ala Asn Leu Asn Gly Thr Ser Arg Lys Val
130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
                180                 185                 190

Asp Ile Tyr Trp Pro Asn Gly Leu Thr Ile Asp Leu Glu Glu Gln Lys
            195                 200                 205

Leu Tyr Trp Ala Asp Ala Lys Leu Ser Phe Ile His Arg Ala Asn Leu
210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
                260                 265                 270

Glu Ile Leu Ser Ala Leu Tyr Ser Pro Met Asp Ile Gln Val Leu Ser
            275                 280                 285

Gln Glu Arg Gln Pro Phe Phe His Thr Arg Cys Glu Glu Asp Asn Gly
290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                325                 330                 335

Lys Ala Gly Ala Glu Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
            355                 360                 365

Val Asp Asp Ile Arg His Ala Ile Ala Ile Asp Tyr Asp Pro Leu Glu
370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
            435                 440                 445

Ser Arg Lys Ile Leu Val Ser Glu Asp Leu Asp Glu Pro Arg Ala Ile
            450                 455                 460

Ala Leu His Pro Val Met Gly Leu Met Tyr Trp Thr Asp Trp Gly Glu
465                 470                 475                 480
```

```
Asn Pro Lys Ile Glu Cys Ala Asn Leu Asp Gly Gln Glu Arg Arg Val
            485                 490                 495
Leu Val Asn Ala Ser Leu Gly Trp Pro Asn Gly Leu Ala Leu Asp Leu
        500                 505                 510
Gln Glu Gly Lys Leu Tyr Trp Gly Asp Ala Lys Thr Asp Lys Ile Glu
            515                 520                 525
Val Ile Asn Val Asp Gly Thr Lys Arg Thr Leu Leu Glu Asp Lys
    530                 535                 540
Leu Pro His Ile Phe Gly Phe Thr Leu Leu Gly Asp Phe Ile Tyr Trp
545                 550                 555                 560
Thr Asp Trp Gln Arg Arg Ser Ile Glu Arg Val His Lys Val Lys Ala
                565                 570                 575
Ser Arg Asp Val Ile Ile Asp Gln Leu Pro Asp Leu Met Gly Leu Lys
            580                 585                 590
Ala Val Asn Val Ala Lys Val Val Gly Thr Asn Pro Cys Ala Asp Arg
        595                 600                 605
Asn Gly Gly Cys Ser His Leu Cys Phe Phe Thr Pro His Ala Thr Arg
    610                 615                 620
Cys Gly Cys Pro Ile Gly Leu Glu Leu Leu Ser Asp Met Lys Thr Cys
625                 630                 635                 640
Ile Val Pro Glu Ala Phe Leu Val Phe Thr Ser Arg Ala Ala Ile His
                645                 650                 655
Arg Ile Ser Leu Glu Thr Asn Asn Asn Asp Val Ala Ile Pro Leu Thr
            660                 665                 670
Gly Val Lys Glu Ala Ser Ala Leu Asp Phe Asp Val Ser Asn Asn His
        675                 680                 685
Ile Tyr Trp Thr Asp Val Ser Leu Lys Thr Ile Ser Arg Ala Phe Met
    690                 695                 700
Asn Gly Ser Ser Val Glu His Val Val Glu Phe Gly Leu Asp Tyr Pro
705                 710                 715                 720
Glu Gly Met Ala Val Asp Trp Met Gly Lys Asn Leu Tyr Trp Ala Asp
                725                 730                 735
Thr Gly Thr Asn Arg Ile Glu Val Ala Arg Leu Asp Gly Gln Phe Arg
            740                 745                 750
Gln Val Leu Val Trp Arg Asp Leu Asp Asn Pro Arg Ser Leu Ala Leu
        755                 760                 765
Asp Pro Thr Lys Gly Tyr Ile Tyr Trp Thr Glu Trp Gly Gly Lys Pro
    770                 775                 780
Arg Ile Val Arg Ala Phe Met Asp Gly Thr Asn Cys Met Thr Leu Val
785                 790                 795                 800
Asp Lys Val Gly Arg Ala Asn Asp Leu Thr Ile Asp Tyr Ala Asp Gln
                805                 810                 815
Arg Leu Tyr Trp Thr Asp Leu Asp Thr Asn Met Ile Glu Ser Ser Asn
            820                 825                 830
Met Leu Gly Gln Glu Arg Val Val Ile Ala Asp Asp Leu Pro His Pro
        835                 840                 845
Phe Gly Leu Thr Gln Tyr Ser Asp Tyr Ile Tyr Trp Thr Asp Trp Asn
    850                 855                 860
Leu His Ser Ile Glu Arg Ala Asp Lys Thr Ser Gly Arg Asn Arg Thr
865                 870                 875                 880
Leu Ile Gln Gly His Leu Asp Phe Val Met Asp Ile Leu Val Phe His
                885                 890                 895
Ser Ser Arg Gln Asp Gly Leu Asn Asp Cys Met His Asn Asn Gly Gln
```

```
                900               905               910
Cys Gly Gln Leu Cys Leu Ala Ile Pro Gly Gly His Arg Cys Gly Cys
            915               920               925
Ala Ser His Tyr Thr Leu Asp Pro Ser Ser Arg Asn Cys Ser Pro Pro
            930               935               940
Thr Thr Phe Leu Leu Phe Ser Gln Lys Ser Ala Ile Ser Arg Met Ile
945               950               955               960
Pro Asp Asp Gln His Ser Pro Asp Leu Ile Leu Pro Leu His Gly Leu
                965               970               975
Arg Asn Val Lys Ala Ile Asp Tyr Asp Pro Leu Asp Lys Phe Ile Tyr
            980               985               990
Trp Val Asp Gly Arg Gln Asn Ile Lys Arg Ala Lys Asp Asp Gly Thr
            995               1000              1005
Gln Pro Phe Val Leu Thr Ser Leu Ser Gln Gly Gln Asn Pro Asp
    1010              1015              1020
Arg Gln Pro His Asp Leu Ser Ile Asp Ile Tyr Ser Arg Thr Leu
    1025              1030              1035
Phe Trp Thr Cys Glu Ala Thr Asn Thr Ile Asn Val His Arg Leu
    1040              1045              1050
Ser Gly Glu Ala Met Gly Val Val Leu Arg Gly Asp Arg Asp Lys
    1055              1060              1065
Pro Arg Ala Ile Val Val Asn Ala Glu Arg Gly Tyr Leu Tyr Phe
    1070              1075              1080
Thr Asn Met Gln Asp Arg Ala Ala Lys Ile Glu Arg Ala Ala Leu
    1085              1090              1095
Asp Gly Thr Glu Arg Glu Val Leu Phe Thr Thr Gly Leu Ile Arg
    1100              1105              1110
Pro Val Ala Leu Val Val Asp Asn Thr Leu Gly Lys Leu Phe Trp
    1115              1120              1125
Val Asp Ala Asp Leu Lys Arg Ile Glu Ser Cys Asp Leu Ser Gly
    1130              1135              1140
Ala Asn Arg Leu Thr Leu Glu Asp Ala Asn Ile Val Gln Pro Leu
    1145              1150              1155
Gly Leu Thr Ile Leu Gly Lys His Leu Tyr Trp Ile Asp Arg Gln
    1160              1165              1170
Gln Gln Met Ile Glu Arg Val Glu Lys Thr Thr Gly Asp Lys Arg
    1175              1180              1185
Thr Arg Ile Gln Gly Arg Val Ala His Leu Thr Gly Ile His Ala
    1190              1195              1200
Val Glu Glu Val Ser Leu Glu Glu Phe Ser Ala His Pro Cys Ala
    1205              1210              1215
Arg Asp Asn Gly Gly Cys Ser His Ile Cys Ile Ala Lys Gly Asp
    1220              1225              1230
Gly Thr Pro Arg Cys Ser Cys Pro Val His Leu Val Leu Leu Gln
    1235              1240              1245
Asn Leu Leu Thr Cys Gly Glu Pro Pro Thr Cys Ser Pro Asp Gln
    1250              1255              1260
Phe Ala Cys Ala Thr Gly Glu Ile Asp Cys Ile Pro Gly Ala Trp
    1265              1270              1275
Arg Cys Asp Gly Phe Pro Glu Cys Asp Asp Gln Ser Asp Glu Glu
    1280              1285              1290
Gly Cys Pro Val Cys Ser Ala Ala Gln Phe Pro Cys Ala Arg Gly
    1295              1300              1305
```

```
Gln Cys Val Asp Leu Arg Leu Arg Cys Asp Gly Glu Ala Asp Cys
    1310                1315                1320

Gln Asp Arg Ser Asp Glu Ala Asp Cys Asp Ala Ile Cys Leu Pro
    1325                1330                1335

Asn Gln Phe Arg Cys Ala Ser Gly Gln Cys Val Leu Ile Lys Gln
    1340                1345                1350

Gln Cys Asp Ser Phe Pro Asp Cys Ile Asp Gly Ser Asp Glu Leu
    1355                1360                1365

Met Cys Glu Ile Thr Lys Pro Pro Ser Asp Asp Ser Pro Ala His
    1370                1375                1380

Ser Ser Ala Ile Gly Pro Val Ile Gly Ile Ile Leu Ser Leu Phe
    1385                1390                1395

Val Met Gly Gly Val Tyr Phe Val Cys Gln Arg Val Val Cys Gln
    1400                1405                1410

Arg Tyr Ala Gly Ala Asn Gly Pro Phe Pro His Glu Tyr Val Ser
    1415                1420                1425

Gly Thr Pro His Val Pro Leu Asn Phe Ile Ala Pro Gly Gly Ser
    1430                1435                1440

Gln His Gly Pro Phe Thr Gly Ile Ala Cys Gly Lys Ser Met Met
    1445                1450                1455

Ser Ser Val Ser Leu Met Gly Gly Arg Gly Gly Val Pro Leu Tyr
    1460                1465                1470

Asp Arg Asn His Val Thr Gly Ala Ser Ser Ser Ser Ser Ser Ser
    1475                1480                1485

Thr Lys Ala Thr Leu Tyr Pro Pro Ile Leu Asn Pro Pro Pro Ser
    1490                1495                1500

Pro Ala Thr Asp Pro Ser Leu Tyr Asn Met Asp Met Phe Tyr Ser
    1505                1510                1515

Ser Asn Ile Pro Ala Thr Ala Arg Pro Tyr Arg Pro Tyr Ile Ile
    1520                1525                1530

Arg Gly Met Ala Pro Pro Thr Thr Pro Cys Ser Thr Asp Val Cys
    1535                1540                1545

Asp Ser Asp Tyr Ser Ala Ser Arg Trp Lys Ala Ser Lys Tyr Tyr
    1550                1555                1560

Leu Asp Leu Asn Ser Asp Ser Asp Pro Tyr Pro Pro Pro Pro Thr
    1565                1570                1575

Pro His Ser Gln Tyr Leu Ser Ala Glu Asp Ser Cys Pro Pro Ser
    1580                1585                1590

Pro Ala Thr Glu Arg Ser Tyr Phe His Leu Phe Pro Pro Pro Pro
    1595                1600                1605

Ser Pro Cys Thr Asp Ser Ser
    1610                1615

<210> SEQ ID NO 6
<211> LENGTH: 1613
<212> TYPE: PRT
<213> ORGANISM: Homo sapiens

<400> SEQUENCE: 6

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

Leu Val Asp Ala Thr Asn Gly Lys Glu Asn Ala Thr Ile Val Val Gly
```

```
            35                  40                  45
Gly Leu Glu Asp Ala Ala Val Asp Phe Val Phe Ser His Gly Leu
     50                  55                  60
Ile Tyr Trp Ser Asp Val Ser Glu Glu Ala Ile Lys Arg Thr Glu Phe
65                  70                  75                  80
Asn Lys Thr Glu Ser Val Gln Asn Val Val Ser Gly Leu Leu Ser
                85                  90                  95
Pro Asp Gly Leu Ala Cys Asp Trp Leu Gly Glu Lys Leu Tyr Trp Thr
            100                 105                 110
Asp Ser Glu Thr Asn Arg Ile Glu Val Ser Asn Leu Asp Gly Ser Leu
            115                 120                 125
Arg Lys Val Leu Phe Trp Gln Glu Leu Asp Gln Pro Arg Ala Ile Ala
            130                 135                 140
Leu Asp Pro Ser Ser Gly Phe Met Tyr Trp Thr Asp Trp Gly Glu Val
145                 150                 155                 160
Pro Lys Ile Glu Arg Ala Gly Met Asp Gly Ser Ser Arg Phe Ile Ile
                165                 170                 175
Ile Asn Ser Glu Ile Tyr Trp Pro Asn Gly Leu Thr Leu Asp Tyr Glu
            180                 185                 190
Glu Gln Lys Leu Tyr Trp Ala Asp Ala Lys Leu Asn Phe Ile His Lys
            195                 200                 205
Ser Asn Leu Asp Gly Thr Asn Arg Gln Ala Val Val Lys Gly Ser Leu
210                 215                 220
Pro His Pro Phe Ala Leu Thr Leu Phe Glu Asp Ile Leu Tyr Trp Thr
225                 230                 235                 240
Asp Trp Ser Thr His Ser Ile Leu Ala Cys Asn Lys Tyr Thr Gly Glu
                245                 250                 255
Gly Leu Arg Glu Ile His Ser Asp Ile Phe Ser Pro Met Asp Ile His
            260                 265                 270
Ala Phe Ser Gln Gln Arg Gln Pro Asn Ala Thr Asn Pro Cys Gly Ile
            275                 280                 285
Asp Asn Gly Gly Cys Ser His Leu Cys Leu Met Ser Pro Val Lys Pro
290                 295                 300
Phe Tyr Gln Cys Ala Cys Pro Thr Gly Val Lys Leu Leu Glu Asn Gly
305                 310                 315                 320
Lys Thr Cys Lys Asp Gly Ala Thr Glu Leu Leu Leu Leu Ala Arg Arg
                325                 330                 335
Thr Asp Leu Arg Arg Ile Ser Leu Asp Thr Pro Asp Phe Thr Asp Ile
            340                 345                 350
Val Leu Gln Leu Glu Asp Ile Arg His Ala Ile Ala Ile Asp Tyr Asp
            355                 360                 365
Pro Val Glu Gly Tyr Ile Tyr Trp Thr Asp Asp Glu Val Arg Ala Ile
            370                 375                 380
Arg Arg Ser Phe Ile Asp Gly Ser Gly Ser Gln Phe Val Val Thr Ala
385                 390                 395                 400
Gln Ile Ala His Pro Asp Gly Ile Ala Val Asp Trp Val Ala Arg Asn
                405                 410                 415
Leu Tyr Trp Thr Asp Thr Gly Thr Asp Arg Ile Glu Val Thr Arg Leu
            420                 425                 430
Asn Gly Thr Met Arg Lys Ile Leu Ile Ser Glu Asp Leu Glu Glu Pro
            435                 440                 445
Arg Ala Ile Val Leu Asp Pro Met Val Gly Tyr Met Tyr Trp Thr Asp
450                 455                 460
```

```
Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
        515                 520                 525

Glu Asp Lys Ile Pro His Ile Phe Gly Phe Thr Leu Leu Gly Asp Tyr
    530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
            580                 585                 590

Ala Glu Glu Asn Gly Gly Cys Ser His Leu Cys Leu Tyr Arg Pro Gln
        595                 600                 605

Gly Leu Arg Cys Ala Cys Pro Ile Gly Phe Glu Leu Ile Ser Asp Met
    610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Asn Val Ala Ile
                645                 650                 655

Pro Leu Thr Gly Val Lys Glu Ala Ser Ala Leu Asp Phe Asp Val Thr
            660                 665                 670

Asp Asn Arg Ile Tyr Trp Thr Asp Ile Ser Leu Lys Thr Ile Ser Arg
        675                 680                 685

Ala Phe Met Asn Gly Ser Ala Leu Glu His Val Val Glu Phe Gly Leu
    690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
        755                 760                 765

Gly Lys Pro Lys Ile Asp Arg Ala Ala Met Asp Gly Ser Glu Arg Thr
    770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
        835                 840                 845

Asp Trp Ser Arg Arg Ser Ile Glu Arg Ala Asn Lys Thr Ser Gly Gln
    850                 855                 860

Asn Arg Thr Ile Ile Gln Gly His Leu Asp Tyr Val Met Asp Ile Leu
865                 870                 875                 880
```

```
Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
        915                 920                 925

Cys Ser Ala Pro Thr Thr Phe Leu Leu Phe Ser Gln Lys Ser Ala Ile
    930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Val Ser Val Pro
        995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Val Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Glu Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
```

```
                    1280            1285            1290
Gln Cys Ala Ser Gly Gln Cys Ile Asp Gly Ala Leu Arg Cys Asn
    1295            1300            1305
Gly Asp Ala Asn Cys Gln Asp Lys Ser Asp Glu Lys Asn Cys Glu
    1310            1315            1320
Val Leu Cys Leu Ile Asp Gln Phe Arg Cys Ala Asn Gly Gln Cys
    1325            1330            1335
Ile Gly Lys His Lys Lys Cys Asp His Asn Val Asp Cys Ser Asp
    1340            1345            1350
Lys Ser Asp Glu Leu Asp Cys Tyr Pro Thr Glu Pro Ala Pro
    1355            1360            1365
Gln Ala Thr Asn Thr Val Gly Ser Val Ile Gly Val Ile Val Thr
    1370            1375            1380
Ile Phe Val Ser Gly Thr Val Tyr Phe Ile Cys Gln Arg Met Leu
    1385            1390            1395
Cys Pro Arg Met Lys Gly Asp Gly Glu Thr Met Thr Asn Asp Tyr
    1400            1405            1410
Val Val His Gly Pro Ala Ser Val Pro Leu Gly Tyr Val Pro His
    1415            1420            1425
Pro Ser Ser Leu Ser Gly Ser Leu Pro Gly Met Ser Arg Gly Lys
    1430            1435            1440
Ser Met Ile Ser Ser Leu Ser Ile Met Gly Gly Ser Ser Gly Pro
    1445            1450            1455
Pro Tyr Asp Arg Ala His Val Thr Gly Ala Ser Ser Ser Ser Ser
    1460            1465            1470
Ser Ser Thr Lys Gly Thr Tyr Phe Pro Ala Ile Leu Asn Pro Pro
    1475            1480            1485
Pro Ser Pro Ala Thr Glu Arg Ser His Tyr Thr Met Glu Phe Gly
    1490            1495            1500
Tyr Ser Ser Asn Ser Pro Ser Thr His Arg Ser Tyr Ser Tyr Arg
    1505            1510            1515
Pro Tyr Ser Tyr Arg His Phe Ala Pro Pro Thr Thr Pro Cys Ser
    1520            1525            1530
Thr Asp Val Cys Asp Ser Asp Tyr Ala Pro Ser Arg Arg Met Thr
    1535            1540            1545
Ser Val Ala Thr Ala Lys Gly Tyr Thr Ser Asp Leu Asn Tyr Asp
    1550            1555            1560
Ser Glu Pro Val Pro Pro Pro Thr Pro Arg Ser Gln Tyr Leu
    1565            1570            1575
Ser Ala Glu Glu Asn Tyr Glu Ser Cys Pro Pro Ser Pro Tyr Thr
    1580            1585            1590
Glu Arg Ser Tyr Ser His His Leu Tyr Pro Pro Pro Ser Pro
    1595            1600            1605
Cys Thr Asp Ser Ser
    1610

<210> SEQ ID NO 7
<211> LENGTH: 5161
<212> TYPE: DNA
<213> ORGANISM: Homo sapiens

<400> SEQUENCE: 7
cgcgcgagga gccgccgccg ccgcgccatg gagcccgagt gagcgcggcg cgggcccgtc      60
cggccgccgg acaacatgga ggcagcgccg cccggggccgc cgtggccgct gctgctgctg     120
```

```
ctgctgctgc tgctggcgct gtgcggctgc ccggcccccg ccgcggcctc gccgctcctg    180
ctatttgcca accgccggga cgtacggctg gtggacgccg cggagtcaa  gctggagtcc    240 accatcgtgg tcagcggcct ggaggatgcg ccgcagtgg  acttccagtt ttccaaggga    300
gccgtgtact ggacagacgt gagcgaggag gccatcaagc agacctacct gaaccagacg    360
ggggccgccg tgcagaacgt ggtcatctcc ggcctggtct ctcccgacgg cctcgcctgc    420
gactgggtgg caagaagct  gtactggacg gactcagaga ccaaccgcat cgaggtggcc    480
aacctcaatg gcacatcccg gaaggtgctc ttctggcagg accttgacca gccgagggcc    540
atcgccttgg accccgctca cgggtacatg tactggacag actggggtga gacgccccgg    600
attgagcggg cagggatgga tggcagcacc cggaagatca ttgtggactc ggacatttac    660
tggcccaatg gactgaccat cgacctggag gagcagaagc tctactgggc tgacgccaag    720
ctcagcttca tccaccgtgc caacctggac ggctcgttcc ggcagaaggt ggtggagggc    780
agcctgacgc  accccttcgc cctgacgctc tccggggaca ctctgtactg gacagactgg    840
cagacccgct ccatccatgc ctgcaacaag cgcactgggg ggaagaggaa ggagatcctg    900
agtgccctct actcacccat ggacatccag gtgctgagcc aggagcggca gcctttcttc    960
cacactcgct gtgaggagga caatggcggc tgctcccacc tgtgcctgct gtccccaagc   1020
gagcctttct acacatgcgc ctgccccacg ggtgtgcagc tgcaggacaa cggcaggacg   1080
tgtaaggcag gagccgagga ggtgctgctg ctggcccggc ggacggacct acggaggatc   1140
tcgctggaca cgccggactt caccgacatc gtgctgcagg tggacgacat ccggcacgcc   1200
attgccatcg actacgaccc gctagagggc tatgtctact ggacagatga cgaggtgcgg   1260
gccatccgca gggcgtacct ggacgggtct ggggcgcaga cgctggtcaa caccgagatc   1320
aacgaccccg atggcatcgc ggtcgactgg gtggcccgaa acctctactg gaccgacacg   1380
ggcacggacc gcatcgaggt gacgcgcctc aacggcacct cccgcaagat cctggtgtcg   1440
gaggacctgg acgagccccg agccatcgca ctgcaccccg tgatgggcct catgtactgg   1500
acagactggg gagagaaccc taaaatcgag tgtgccaact ggatgggca  ggagcggcgt   1560 gtgctggtca atgcctccct cgggtggccc aacggcctgg ccctgaccct gcaggagggg   1620
aagctctact ggggagacgc caagacagag aagatcgagg tgatcaatgt tgatgggacg   1680
aagaggcgga ccctcctgga ggacaagctc ccgcacattt ttgggttcac gctgctgggg   1740
gacttcatct actggactga ctggcagcgc gcagcatcg  agcgggtgca caaggtcaag   1800
gccagccggg acgtcatcat tgaccagctg cccgacctga tggggctcaa agctgtgaat   1860
gtggccaagg tcgtcggaac caacccgtgt gcggacagga cgggggggtg cagccacctg   1920
tgcttcttca cccccacgc  aaccccggtgt ggctgcccca tcggcctgga gctgctgagt   1980
gacatgaaga cctgcatcgt gcctgaggcc ttcttggtct tcaccagcag agccgccatc   2040
cacaggatct ccctcgagac caataacaac gactgtgcca tcccgctcac gggcgtcaag   2100
gaggcctcag ccctggactt tgatgtgtcc aacaaccaca tctactggac agacgtcagc   2160
ctgaagacca tcagccgcgc cttcatgaac gggagctcgg tggagcacgt ggtgagttt    2220 ggccttgact accccgaggg catggccgtt gactggatgg caagaacct  ctactgggcc   2280 gacactggga ccaacagaat cgaagtggcg cggctggacg ggcagttccg gcaagtcctc   2340
gtgtggaggg acttggacaa cccgaggtcg ctggccctgg atcccaccaa gggctacatc   2400
tactggaccg agtggggcgg caagccgagg atcgtgcggg ccttcatgga cgggaccaac   2460
```

```
tgcatgacgc tggtggacaa ggtgggccgg gccaacgacc tcaccattga ctacgctgac    2520
cagcgcctct actggaccga cctggacacc aacatgatcg agtcgtccaa catgctgggt    2580
caggagcggg tcgtgattgc cgacgatctc ccgcacccgt tcggtctgac gcagtacagc    2640
gattatatct actggacaga ctggaatctg cacagcattg agcgggccga caagactagc    2700
ggccggaacc gcaccctcat ccagggccac ctggacttcg tgatggacat cctggtgttc    2760
cactcctccc gccaggatgg cctcaatgac tgtatgcaca acaacgggca gtgtgggcag    2820
ctgtgccttg ccatccccgg cggccaccgc tgcggctgcg cctcacacta caccctggac    2880
cccagcagcc gcaactgcag cccgcccacc accttcttgc tgttcagcca gaaatctgcc    2940
atcagtcgga tgatcccgga cgaccagcac agcccggatc tcatcctgcc cctgcatgga    3000
ctgaggaacg tcaaagccat cgactatgac ccactggaca agttcatcta ctgggtggat    3060
gggcgccaga acatcaagcg agccaaggac gacgggaccc agccctttgt tttgacctct    3120
ctgagccaag gccaaaaccc agacaggcag ccccacgacc tcagcatcga catctacagc    3180
cggacactgt tctggacgtg cgaggccacc aataccatca cgtccacag gctgagcggg    3240 gaagccatgg gggtggtgct gcgtggggac cgcgacaagc ccagggccat cgtcgtcaac    3300
gcggagcgag ggtacctgta cttcaccaac atgcaggacc gggcagccaa gatcgaacgc    3360
gcagccctgg acggcaccga gcgcgaggtc ctcttcacca ccggcctcat ccgccctgtg    3420
gccctggtgg tggacaacac actgggcaag ctgttctggg tggacgcgga cctgaagcgc    3480
attgagagct gtgacctgtc aggggccaac cgcctgaccc tggaggacgc caacatcgtg    3540
cagcctctgg gcctgaccat ccttggcaag catctctact ggatcgaccg ccagcagcag    3600
atgatcgagc gtgtggagaa gaccaccggg acaagcggac tcgcatcca gggccgtgtc    3660 gcccacctca ctggcatcca tgcagtggag gaagtcagcc tggaggagtt ctcagcccac    3720
ccatgtgccc gtgacaatgg tggctgctcc cacatctgta ttgccaaggg tgatgggaca    3780
ccacggtgct catgcccagt ccacctcgtg ctcctgcaga acctgctgac ctgtggagag    3840
ccgcccacct gctccccgga ccagtttgca tgtgccacag gggagatcga ctgtatcccc    3900
ggggcctggc gctgtgacgg cttttcccgag tgcgatgacc agagcgacga ggagggctgc    3960
cccgtgtgct ccgccgccca gttcccctgc gcgcggggtc agtgtgtgga cctgcgcctg    4020
cgctgcgacg gcgaggcaga ctgtcaggac cgctcagacg aggcggactg tgacgccatc    4080
tgcctgccca accagttccg gtgtgcgagc ggccagtgtg tcctcatcaa acagcagtgc    4140
gactccttcc ccgactgtat cgacggctcc gacgagctca tgtgtgaaat caccaagccg    4200
ccctcagacg acagcccggc ccacagcagt gccatcgggc ccgtcattgg catcatcctc    4260
tctctcttcg tcatgggtgg tgtctatttt gtgtgccagc gcgtggtgtg ccagcgctat    4320
gcgggggcca acgggccctt cccgcacgag tatgtcagcg gaccccgca cgtgcccctc    4380 aatttcatag ccccgggcgg ttcccagcat ggccccttca caggcatcgc atgcggaaag    4440
tccatgatga gctccgtgag cctgatgggg gccggggcg gggtgcccct ctacgaccgg    4500
aaccacgtca caggggcctc gtccagcagc tcgtccagca cgaaggccac gctgtacccg    4560
ccgatcctga acccgccgcc ctccccgcc acggaccct ccctgtacaa catgacatg    4620 ttctactctt caaacattcc ggccactgcg agaccgtaca ggccctacat cattcgagga    4680
atggcgcccc cgacgacgcc ctgcagcacc gacgtgtgtg acagcgacta cagcgccagc    4740
cgctggaagg ccagcaagta ctacctggat ttgaactcgg actcagaccc ctatccaccc    4800
ccacccacgc cccacagcca gtacctgtcg gcggaggaca gctgcccgcc ctcgcccgcc    4860
```

```
accgagagga gctacttcca tctcttcccg cccccctccgt cccccctgcac ggactcatcc    4920 tgacctcggc cgggccactc tggcttctct gtgcccctgt aaatagtttt aaatatgaac    4980
aaagaaaaaa atatatttta tgatttaaaa aataaatata attgggattt taaaaacatg    5040
agaaatgtga actgtgatgg ggtgggcagg gctgggagaa cttttgtacag tggagaaata    5100 tttataaact taattttgta aaacagaaaa aaaaaaaaaa aaaaaaaaaa aaaaaaaaa     5160 a                                                                     5161

<210> SEQ ID NO 8
<211> LENGTH: 10088
<212> TYPE: DNA
<213> ORGANISM: Homo sapiens

<400> SEQUENCE: 8
gtgccccttt ctttcttctc tcgctgggaa gctgggaagt atgagcgtgc agccctgccg     60
ctgcggcggc cgccccggct cctcgcctcc cccacttctg gccacccctc gccggtgaga   120
gaagagaacg cgagaaggga agatgggggc cgtcctgagg agcctcctgg cctgcagctt   180
ctgtgtgctc ctgagagcgg ccccctttgtt gctttatgca aacagacggg acttgcgatt   240
ggttgatgct acaaatggca aagagaatgc tacgattgta gttggaggct ggaggatgc    300 agctgcggtg gactttgtgt ttagtcatgg cttgatatac tggagtgatg tcagcgaaga   360
agccattaaa cgaacagaat ttaacaaaac tgagagtgtg cagaatgttg ttgtttctgg   420
attattgtcc cccgatgggc tggcatgtga ttggcttgga gaaaaattgt actggacaga   480
ttctgaaact aatcggattg aagtttctaa tttagatgga tctttacgaa aagttttatt   540
ttggcaagag ttggatcaac ccagagctat tgccttagat ccttcaagtg ggttcatgta   600
ctggacagac tggggagaag tgccaaagat agaacgtgct ggaatggatg gttcaagtcg   660
cttcattata ataaacagtg aaatttactg gccaaatgga ctgactttgg attatgaaga   720
acaaaagctt tattgggcag atgcaaaact taatttcatc cacaaatcaa atctggatgg   780
aacaaatcgg caggcagtgg ttaaaggttc ccttccacat cctttttgcct tgacgttatt   840 tgaggacata ttgtactgga ctgactggag cacacactcc attttggctt gcaacaagta   900
tactggtgag ggtctgcgtg aaatccattc tgacatcttc tctcccatgg atatacatgc   960
cttcagccaa cagaggcagc aaatgccaca aatccatgt ggaattgaca atgggggttg    1020
ttcccatttg tgtttgatgt ctccagtcaa gccttttta cagtgtgctt gccccactgg   1080
ggtcaaactc ctgagaatg gaaaaacctg caaagatggt gccacagaat tattgctttt   1140
agctcgaagg acagacttga gacgcatttc tttggataca ccagattta cagacattgt    1200 tctgcagtta gaagacatcc gtcatgccat tgccatagat tacgatcctg tggaaggcta   1260
catctactgg actgatgatg aagtgagggc catacgccgt tcatttatag atggatctgg   1320
cagtcagttt gtggtcactg ctcaaattgc ccatcctgat ggtattgctg tggactgggt   1380
tgcacgaaat ctttattgga cagacactgg cactgatcga atagaagtga caaggctcaa   1440
tgggaccatg aggaagatct tgatttcaga ggacttagag gaaccccggg ctattgtgtt   1500 agatccatg ttgggtaca tgtattggac tgactgggga gaaattccga aaattgagcg    1560
agcagctctg gatggttctg accgtgtagt attggttaac acttctcttg gttggccaaa   1620
tggtttagcc ttggattatg atgaaggcaa aatatactgg ggagatgcca aaacagacaa   1680
gattgaggtt atgaatactg atggcactgg gagacgagta ctagtggaag acaaaattcc   1740
```

```
tcacatattt ggatttactt tgttgggtga ctatgtttac tggactgact ggcagaggcg    1800
tagcattgaa agagttcata aacgaagtgc agagagggaa gtgatcatag atcagctgcc    1860
tgacctcatg ggcctaaagg ctacaaatgt tcatcgagtg attggttcca acccctgtgc    1920
tgaggaaaac gggggatgta gccatctctg cctctataga cctcagggcc ttcgctgtgc    1980
ttgccctatt ggctttgaac tcatcagtga catgaagacc tgcattgtcc cagaggcttt    2040 cctttttgttt tcacggagag cagatatcag acgaatttct ctggaaacaa acaataataa   2100
tgtggctatt ccactcactg gtgtcaaaga agcttctgct ttggattttg atgtgacaga    2160
caaccgaatt tattggactg atatatcact caagaccatc agcagagcct ttatgaatgg    2220
cagtgcactg gaacatgtgg tagaattcgg cttagattat ccagaaggca tggcagtaga    2280
ctggcttggg aagaacttgt actgggcaga cacaggaacg aatcgaattg aggtgtcaaa    2340
gttggatggg cagcaccgac aagttttggt gtggaaagac ctagatagtc ccagagctct    2400
cgcgttggac cctgccgaag gatttatgta ttggactgaa tggggtggaa aacctaagat    2460
agacagagct gcaatggatg gaagtgaacg tactaccctta gttccaaatg tggggcgggc    2520
aaacggccta actattgatt atgctaaaag gaggctttat tggacagacc tggacaccaa    2580
cttaatagaa tcttcaaata tgcttgggct caaccgtgaa gttatagcag atgacttgcc    2640
tcatcctttt ggcttaactc agtaccaaga ttatatctac tggacggact ggagccgacg    2700
cagcattgag cgtgccaaca aaccagtgg ccaaaaccgc accatcattc agggccattt    2760
ggattatgtg atggacatcc tcgtctttca ctcatctcga cagtcagggt ggaatgaatg    2820
tgcttccagc aatgggcact gctcccacct ctgcttggct gtgccagttg ggggttttgt    2880
ttgtggatgc cctgcccact actctcttaa tgctgacaac aggacttgta gtgctcctac    2940
gactttcctg ctcttcagtc aaaagagtgc catcaaccgc atggtgattg atgaacaaca    3000
gagccccgac atcatccttc ccatccacag ccttcggaat gtccgggcca ttgactatga    3060
cccactggac aagcaactct attggattga ctcacgacaa acatgatcc gaaaggcaca    3120 agaagatggc agccagggct ttactgtggt tgtgagctca gttccgagtc agaacctgga    3180
aatacaaccc tatgacctca gcattgatat ttacagccgc tacatctact ggacttgtga    3240
ggctaccaat gtcattaatg tgacaagatt agatgggaga tcagttggag tggtgctgaa    3300
aggcgagcag gacagacctc gagccgttgt ggtaaaccca gagaaagggt atatgtattt    3360
taccaatctt caggaaaggt ctcctaaaat tgaacgggct gctttggatg ggacagaacg    3420
ggaggtcctc ttttcagtg gcttaagtaa accaattgct ttagccccttg atagcaggct    3480 gggcaagctc ttttgggctg attcagatct ccggcgaatt gaaagcagtg atctctcagg    3540
tgctaaccgg atagtattag aagactccaa tatcttgcag cctgtgggac ttactgtgtt    3600
tgaaaactgg ctctattgga ttgataaaca gcagcaaatg attgaaaaaa ttgacatgac    3660
aggtcgagag ggtagaacca agtccaagc tcgaattgcc cagcttagtg acattcatgc    3720
agtaaaggag ctgaaccttc aagaatacag acagcaccct tgtgctcagg ataatggtgg    3780
ctgttcacat atttgtcttg taaaggggga tggtactaca aggtgttctt gccccatgca    3840
cctggttcta cttcaagatg agctatcatg tggagaacct ccaacatgtt ctcctcagca    3900
gtttacttgt ttcacgggg aaattgactg tatccctgtg gcttggcggt gcgatgggtt    3960
tactgaatgt gaagaccaca gtgatgaact caattgtcct gtatgctcag agtcccagtt    4020
ccagtgtgcc agtgggcagt gtattgatgg tgccctccga tgcaatggag atgcaaactg    4080
ccaggacaaa tcagatgaga agaactgtga agtgctttgt ttaattgatc agttccgctg    4140
```

```
tgccaatggt cagtgcattg gaaagcacaa gaagtgtgat cataatgtgg attgcagtga   4200
caagtcagat gaactggatt gttatccgac tgaagaacca gcaccacagg ccaccaatac   4260
agttggttct gttattggcg taattgtcac cattttgtg tctggaactg tatactttat    4320
ctgccagagg atgttgtgtc cacgtatgaa gggagatggg gaaactatga ctaatgacta   4380
tgtagttcat ggaccagctt ctgtgcctct tggttatgtg ccacacccaa gttctttgtc   4440
aggatctctt ccaggaatgt ctcgaggtaa atcaatgatc agctccctca gtatcatggg   4500
gggaagcagt ggaccccct atgaccgagc ccatgttaca ggagcatcat caagtagttc     4560
ttcaagcacc aaaggcactt acttccctgc aattttgaac cctccaccat ccccagccac   4620
agagcgatca cattacacta tggaatttgg atattcttca aacagtcctt ccactcatag   4680
gtcatacagc tacaggccat atagctaccg gcactttgca ccccccacca cacccctgcag  4740 cacagatgtt tgtgacagtg actatgctcc tagtcggaga atgacctcag tggcaacagc   4800
caagggctat accagtgact gaactatga ttcagaacct gtgcccccac ctcccacacc     4860
ccgaagccaa tacttgtcag cagaggagaa ctatgaaagc tgcccacctt ctccatacac   4920
agagaggagc tattctcatc acctctaccc accgccaccc tctccctgta cagactcctc   4980
ctgaggaggg gccctcctcc tctgactgcc tccaacgtaa aaatgtaaat ataaatttgg   5040
ttgagatctg gagggggga gggagctatt agagaaggat gaggcagacc atgtacagtt    5100
aaaattataa aatggggtag ggaatactgg agatatttgt acagaagaaa aggatattta   5160
tatattttct taaacagca gatttgctgc ttgtgccata aaagtttgta taaaaaaaat    5220
ttgtactaaa agttttattt ttgcaaacta aatacacaaa gcatgcctta aacccagtga   5280
agcaactgag tacaaaggaa acaggaataa taaaggcatc actgaccagg aatatctggg   5340
ctttattgat accaaaaata aaaagagga agaagaaaaa ttaagtccat ctcagagcag    5400
caaaccatag atacatggat gtagccagat agccttcagt taactaacat ttgagggcca   5460
acaagtaaga aatgatgaaa ggaaaaaat gcaattaata ctaaccttgg acgaagggct    5520
ttgttttctc taggaatcca acagtgctag tgaggaaagt agatatttct aaaaacccat   5580
tctgggtgtt gctgttgtag gagagatcag ccctctggta agatgccatg aagctgtgtg   5640
tgtgtgcaag tctctgtccc tacctttaga atccatacct ctgtcaaaat gaattttttt   5700
ctctaggtat gtttaccttg ctgcctcctc cagcaacttg gtaagtcatt ttgctaagat   5760
accatgattt ttttaagctg aagcattgac taaatggaat tttctaaatt aaacttgatt   5820
ttaatatttc ttctagctcc attccccagt aggcttagct cttcaatttg actgctgttt   5880
ttgcataatg atcaaaagtt agacatatta tttctcttct tccaagattg ttttaatgct   5940
cattaaaatg tctttttaca acacatatag acaatgttta agaattaaaa atttaaccat   6000 tatgttttg ttgtaaatct catatccttg cactactttc agcatatatc acagtacgaa     6060
atcatttata tatatatata tatatatata tatatatata tatatatata tatatatatt   6120
ttgtttgttt gtttgttttc tgagtaaaac atttaaatat gttctggtta gagacaatct   6180
atttaaaaag attttttct tattaggatt ttccctatat taacagtttg tgatgttttc    6240
atgttcttta daccggtttt tctcagaata atgtctacat acatacctct tctaatgtgt   6300
gacatgaatt taatatcttt ctgttaccca ctgtgaatgt taggctgttt tcaaattatc   6360
cacaaattat tcttgtaatc acccaatatt tttatgtggg tcctctctta cccattatgg  6420
attaagatag tttaacaaat ttaacaatga ggattaaatg agaaggcaaa ctgttaactt   6480
```

-continued

```
ctcagctgtc agaatttggg tggaagggaa taatggaagc ctcttttgtg atctgcctga    6540
cctgctgtca tgtatggtac tggggctgct acatcttgag ctatcagggc tgacctgtgg    6600
aatgattcta gcacttgctc tgccaccttg ccagaagttc gtttcctgct ttttacacat    6660
gtgtagcact tctctgctaa aattgaatgg ttttaaacta atgtattttt agcttaagag    6720
gtgttggtca gttaattatt gaattttttt tttttctttt ttaattctgt cttgccaagg    6780
cctctctggg tttcagggcc caagagaaaa cagtggaaga aaggattcag atttgggca    6840 agggtgaagt aactgttcat gcaagttaaa aatacctaag taaagttttt gaagataaaa    6900
ttgtggtttc agaataatgc tgattgttgg agactgtaag aatcaggtgc acttgatttt    6960
gcatataagc aaatggtaaa tctatcagaa tcctaaaaca gacaagcatg aactcttccc    7020
attgctggaa ctaagtgccc acagtgtcag acaaaatgga cattgaactt ggattctgtg    7080
atacacaggg cacttgatgc ttaaatgaag atggaaaggt tagcaatacc tgggtgtcag    7140
ttagaatttg agaattctat atgtttacat atttaaatgt gcatcttgat ctggtgggct    7200
tcccatgtgg agacttgcac tctaattaac taagaagaat attgccttgt tggatctcag    7260
tccacgtgct tgcactgcga tggcaatggc ctcttcttca aaatactaat ttgtgtgcca    7320
atttgtttaa aattatttga aggcagttca gcctaatctc agtgttctct ttctggggta    7380
gatgagatgg attcttaata tttctgggag tacttttaa tgagagaatt gtcaaatttg    7440
gaaagattta ttgagcctta ggttacatgg acagttaagc ttaagtaaac tgtatattga    7500
ttatcaaaca caagctgtaa ttggaaaagt tgagaggaaa agcatgagat cacaaattag    7560
ggggaaaaaa gaaaagggat ttttaaattt ggtgtattaa attcattgtc caaggggaa    7620 aatgaataat gtttcattag attccttata tgcaaaagta tttattttga acatgtgtcc    7680
taaaatatat gcactaactg atgtgattaa aattgtccaa gaaataaact tgagcataac    7740
atactttgtg tgcaccacag taagctattc tgcattgaag tggtctttta taactaaggc    7800
ctggactttg ctccaacaga gtcgtggtct tctgaatagt gacttaagga gttttgtttg    7860
cttaagtcag ataatagcac attcacaggg aaacaaagag agttggtgga tagaattttc    7920
tgactattaa ttttcttcc atgaaatttt attatgcctt tggcactttc tgccactctt    7980
acagcatatc acaagatatc tgtttagcag aagattatgt agttacttta attttaatat    8040
aaaagtagct tgtgatacat taccaagaga tctctgattc tttagtaagt ttgagaacac    8100
ctattctaca gagatgatag gtacttagaa atgaagactt taaagtacat tttaatctaa    8160
tataggccag taattggggg aagggctttg gagcagtaca attttaagat gattttgagg    8220
gttgtatttc tttatcattt aaaaatatcc taaagtcagt aatttatatg aaggaaactc    8280
attcattatt gaaggtatta aaaatagcca tcatctgtat taggtagcag ttttggagga    8340
tcatcttttt cttttgctat aaagccctat taatgaagaa tacttccagt agagttaata    8400
gctgtagctt acctagtgtg ttaatgaagt gtgtttattt atgtgacttg ataccagtag    8460
tcataataga gactgaagag gtatgcgtta agcacgccta cttctatgca gtaaacaggc    8520
tgcagctgcc tagattagat tcttagaaat gtcatatttt gaattgtttt atttcttgta    8580
ggggaagctt tgtcccactt cattcatttg catgccatag gaattacata ttggttatca    8640
ttacgtatct aacaagattc agaaacaaaa atcttggact tttcacatcc gaaatatgtc    8700
agctcttaat aaatgtgtgg tgcttaagtc tacatatggc atccatagtt gatttagagt    8760
atggatatga gtgtgttgac cagttatcag taggtggaca aatatttggg catctacaga    8820
tgagactatg cactaagtgt ggactgagtc ctaaagaagc ttatagtcag gtgttgttta    8880
```

```
aaacattatc agaattctta aacccaagga atttaatttt atttggtatt tcttaagcct    8940
aaaatgaacc aagagaaaga tgattttaga aagtacttgt agtgaaagat gattttagaa    9000
agtacttgta gtgcatgtgt ggcttctgac ttttgggatg gcaccatttt ataatagttt    9060
caaaatttag cttttgaaat tctcaacatt ttatggtaga agactttgga cctcaagtat    9120
aaaattatac gtttataatt tttttaaaat ttaaattata agtattgtga attcacactc    9180
tcaggctatt gtctgacttg atctacgtct cataaagcct gtacctgagt ggagtggaag    9240
gtggagtctt aggttaatca gttactgact ctaccctcac cctctttcaa ttgaggtaaa    9300
ctttgctgtt tttcttttc ataaagcatt ctcaaattgt tgagtttatt gctgaaaaaa     9360
atctccatga ctttacagat agaattacaa actaaatgat gtcttgtatt tagaagcaga    9420
gtacagacct aacgaactgt tagattctcc accatcactt agggtttgcc cagaagcaac    9480
accagagaat tacagacaac gcgcttttgc tgaactgtcc attttggtgg ttgtgttttt    9540
cagtcaaata taagcaggat gggcgataga gatatattta tatatagata catattctat    9600
atatctaatg cctaaatatg ggtattaaag ggaaaatttt taaagtctga ttaaatccaa    9660
tatgacatga aattaaatat atggattagt aaggaaaaat gttaaaaagt agagaggata    9720
ccaagaagat taaactggac tagccttatt tgcaagtgaa ggatctggtg ctgctttcag    9780
atgtttatct tttattttt tcccttaagc tttaatcttc gtcattgtct taaagtcaac     9840
tggtgtttct tgttcattga ctttggtacg atggtgcttt gcaaggatgt atttatgtta    9900
taatggccaa catttggtca gcccttgtcc acttattcac ttccctcctt ttgtaaaata    9960
agtgctttaa ttataaactg tataaaaata ccttgtataa accccttttt tgattattac   10020
aataaataag ctgaattgta acaaatgaaa tttgatttt gtaataaaac agtggaaaag    10080
taaaaaaa                                                            10088
```